(12) United States Patent  (10) Patent No.: US 8,530,483 B2
Barrow et al.  (45) Date of Patent: Sep. 10, 2013

(54) SUBSTITUTED AZABENZOXAZOLES

(75) Inventors: James C. Barrow, Arnold, MD (US);
Scott Harrison, Etkins Park, PA (US);
James Mulhearn, Saint Davids, PA (US); Cyrille Sur, Harleysville, PA (US); David L. Williams, Telford, PA (US); Scott Wolkenberg, Jenkintown, PA (US); Eric Hostetler, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 169 days.

(21) Appl. No.: 12/995,314

(22) PCT Filed: May 28, 2009

(86) PCT No.: PCT/US2009/045376
§ 371 (c)(1),
(2), (4) Date: Nov. 30, 2010

(87) PCT Pub. No.: WO2009/155017
PCT Pub. Date: Dec. 23, 2009

(65) Prior Publication Data
US 2011/0085985 A1  Apr. 14, 2011

Related U.S. Application Data

(60) Provisional application No. 61/130,399, filed on May 30, 2008, provisional application No. 61/198,022, filed on Oct. 31, 2008.

(51) Int. Cl.
| A01N 43/90 | (2006.01) |
| A01N 43/42 | (2006.01) |
| A61K 31/519 | (2006.01) |
| A61K 31/44 | (2006.01) |
| C07D 239/00 | (2006.01) |
| C07D 471/00 | (2006.01) |
| C07D 491/00 | (2006.01) |
| C07D 513/02 | (2006.01) |
| C07D 515/02 | (2006.01) |
| C07D 471/02 | (2006.01) |
| C07D 491/02 | (2006.01) |
| C07D 498/02 | (2006.01) |

(52) U.S. Cl.
USPC ........ 514/260.1; 514/301; 514/302; 544/255; 546/114; 546/115

(58) Field of Classification Search
USPC ........... 514/258.1, 301, 302, 260.1; 544/255; 546/114, 115; 549/32, 462
See application file for complete search history.

(56) References Cited

U.S. PATENT DOCUMENTS

| 3,899,506 | A | 8/1975 | Shen et al. |
| 4,038,396 | A * | 7/1977 | Shen et al. .................... 514/302 |
| 6,001,331 | A | 12/1999 | Caprathe et al. |
| 6,696,039 | B2 | 2/2004 | Kung et al. |
| 2004/0131545 | A1 | 7/2004 | Kung et al. |
| 2005/0043377 | A1 | 2/2005 | Klunk et al. |
| 2008/0299041 | A1 | 12/2008 | Jeong et al. |

FOREIGN PATENT DOCUMENTS

| WO | WO0216333 | 2/2002 |
| WO | WO02085903 | 10/2002 |
| WO | WO03048137 | 6/2003 |
| WO | WO2004032975 | 4/2004 |
| WO | WO2004064869 | 8/2004 |
| WO | WO2004083195 | 9/2004 |
| WO | WO2006044503 | 4/2006 |
| WO | WO2007002540 | 1/2007 |
| WO | WO2007033080 | 3/2007 |
| WO | WO2007035405 | 3/2007 |
| WO | WO2007/074786 | 5/2007 |
| WO | WO2007070173 | 6/2007 |
| WO | WO2007086800 | 8/2007 |

(Continued)

OTHER PUBLICATIONS

Flouzat et. al., Synthesis, 1990, Thieme, vol. 1, pp. 64-66.*

(Continued)

*Primary Examiner* — Sreeni Padmanabhan
*Assistant Examiner* — Sarah Pihonak
(74) *Attorney, Agent, or Firm* — Sylvia A. Ayler; Gerard M. Devlin

(57) ABSTRACT

The present invention relates to novel amyloid binding compounds of formula (I) and methods for measuring effects of the compounds, by measuring changes of amyloid plaque level in living patients. More specifically, the present invention relates to a method of using the compounds of this invention as tracers in positron emission tomography (PET/) imaging to study amyloid deposits in brain in vivo to allow diagnosis of Alzheimer's disease. Thus, the present invention relates to use of the novel amyloid binding compounds as a diagnostic. The invention further relates to a method of measuring clinical efficacy of Alzheimer's disease therapeutic agents. Specifically, the present invention relates to novel aryl or heteroaryl substituted azabenzoxazole derivatives, compositions, and therapeutic uses and processes for making such compounds, or a pharmaceutically acceptable salt, solvate or in vivo hydrolysable ester thereof, wherein: X is O or S; A and Y independently are N, or CH.

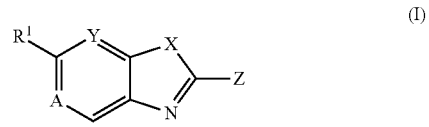

13 Claims, No Drawings

(56) References Cited

FOREIGN PATENT DOCUMENTS

| | | |
|---|---|---|
| WO | WO2007149030 | 12/2007 |
| WO | WO2008108729 | 9/2008 |
| WO | WO2008108730 | 9/2008 |

OTHER PUBLICATIONS

Jue et. al., Magnetic Resonance in Medicine, 1987, Academic Press, vol. 5, pp. 377-379.*

Falco et. al., Journal of the American Chemical Society, 1950, American Chemical Society, vol. 72, pp. 3203-3205.*

Falco et. al., Journal of the American Chemical Society, 1952, American Chemical Society, vol. 74, pp. 4897-4902.*

Cai et al., Radioligand Development for PET Imaging of Beta-Amyloid (A Beta)—Current Status, Current Medicinal Chemistry, 2007, vol. 14, pp. 19-52.

Chandra et al., New Diphenylacetylenes as Probes for Positron Emission Tomographic Imaging of Amyloid Plaques, J. Med. Chem., 2007, vol. 50, pp. 2415-2423.

Qu et al. "Quick Assembly of 1,4-Diphenyltriazoles as Probes Targeting Beta-Amyloid Aggregates in Alzheimer's Disease", 2007, vol. 50, pp. 3380-3387.

Cai et al., "Synthesis and Structure-Affinity Relationships of new 4-)6-Iodo-H-Imidao[1,2-a] Pyridin-2-yl-N-Dimethylbenzeneamine Derivatives as Ligands for Humbn-Beta-Amyloid Plaques", J. Med. Chem, 2007, vol. 50, pp. 4746-4758.

Miller, "A Better View of Brain Disorders", 2006, Science, vol. 313, pp. 1376-1379.

Coimbra et al., "The Role of MRI and PET/SPECT in Alzheimer's Disease", Current Topics in Medicinal Chemistry, 2006, vol. 6, pp. 629-647.

Nordberg, "PET Imaging of Amyloid in Alzheimer's Disease", Neurology, vol. 3, 2004, pp. 519-527.

Mathis et al., "Synthesis and Evaluation of C-Labeled 6-Substitut4ed 2-Arylbenzothiazoles as Amyloid Imaging Agents", J. Med. Chem, 2003, vol. 46, pp. 2740-2754.

Klunk et al, "Imaging Brain Amyloid in Alzheimer's Disease with Pittsburgh Compound-B", Neurological Association, 2004, pp. 306-318.

Shoghi-Jadid et al., "Localization of Neurofibrillary Tangles and Beta-Amyloid Plaques in the Brains of Living Patients with Alzheimer Disease",, Am. J. Geriatric Psychiatry, 2002, vol. 10, pp. 24-35.

Berge et al., "Pharmaceutical Salts", J. Pharmaceutical Sciences, 1977, vol. 66, pp. 1-19.

Eliel et al., "Chirality in Molecules Devoid of Chiral Centers", Stereochemistry of Organic Compounds, Chapter 14, pp. 1119-1190, 1994.

Zhuang et al., "Ibox (2-(4-Dimethylaminophneyl)-6-Idoobenzoxazole): A Ligand for Imaging Amyloid Plaques in the Brain", Nuclear Medicine and Biology, 2001, vol. 28, pp. 889.

Clark et al., "2-(Substituted Phenyl) Oxazolo [4,5-b] Pyridines and 2-(Substituted Phenyl) Oxazolo [5,4-b] Pyridines as Non acidic Antiinflammatory Agents", J. of Medicinal Chemistry, 1978, vol. 21, pp. 1158-1162.

Isomura et al., "Studies on the Synthesis and Anti-Inflammatory Activity of 2,6-Di-Tert-Butylphenols with a Heterocyclic Group at the 40-Position", Chemical & Pharmaceutical Bulletin, 1983, vol. 31, pp. 3168-3178.

Aletenhoff et al., "A Domino Copper-Catalysed C-N and C0 Cross-Coupling for the Conversion of Primary Amides into Benzoxazoles", Advanced Synthesis & Catalysis, Advanced Synthesis & Catalysis, 2004, vol. 346, pp. 1661-1664.

Qu et al., "Novel Styrylpyridines as Probes for SPECT Imaging of Amyloid Plaques", J. Med. Chem, 2007, vol. 50, pp. 2157-2165.

\* cited by examiner

US 8,530,483 B2

SUBSTITUTED AZABENZOXAZOLES

CROSS REFERENCE TO RELATED APPLICATIONS

This application is the National Stage of International Application No. PCT/US2009/045376 filed on May 28, 2009, which claims the benefit under 35 U.S.C. 119(e) of U.S. Provisional Application Nos. 61/130,339 and 61/198,022 filed May 30, 2008 and Oct. 31, 2009 respectively.

FIELD OF THE INVENTION

The present invention relates to novel aryl or heteroaryl substituted azabenzoxazole derivatives, compositions, and therapeutic uses and processes for making such compounds. The invention is further directed to $^2H$, $^3H$, $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{76}Br$, $^{77}Br$, $^{123}I$, $^{124}I$ and $^{131}I$ isotopically labeled aryl or heteroaryl substituted azabenzoxazole derivative compounds. In particular, the present invention is directed to $^{11}C$, $^{13}C$, $^{14}C$, $^{18}F$, $^{15}O$, $^{13}N$, $^{35}S$, $^2H$, and $^3H$ isotopes of aryl or heteroaryl substituted azabenzoxazoles and methods of their preparation.

The invention also relates to novel aryl or heteroaryl substituted azabenzoxazole derivatives which are suitable for imaging amyloid deposits in living patients. More specifically, the present invention relates to a method of using the compounds of this invention as tracers in positron emission tomography (PET) imaging to study amyloid deposits in brain in vivo to allow diagnosis of Alzheimer's disease. The invention further relates to a method of measuring clinical efficacy of Alzheimer's disease therapeutic agents.

BACKGROUND OF THE INVENTION

Noninvasive nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain info ration on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

For noninvasive in vivo imaging, compounds can be labeled with either positron- or gamma-emitting radionuclides. The most commonly used positron emitting (PET) radionuclides are $^{11}C$, $^{18}F$, $^{15}O$ and $^{13}N$, all of which are accelerator produced, and have half-lives of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and most hospitals worldwide. The most widely used of these are $^{99}Tc$, $^{201}Tl$ and $^{123}I$.

In a typical PET study, a small amount of radiotracer is administered to the experimental animal, normal human or patient being tested. The radiotracer then circulates in the blood of the subject and may be absorbed in certain tissues. The radiotracer may be preferentially retained in some of these tissues because of specific enzymatic conversion or by specific binding to macromolecular structures such as proteins. Using sophisticated imaging instrumentation to detect positron emission, the amount of radiotracer is then non-invasively assessed in the various tissues in the body. The resulting data are analyzed to provide quantitative spatial information of the in vivo biological process for which the tracer was designed. PET gives pharmaceutical research investigators the capability to assess biochemical changes or metabolic effects of a drug candidate in vivo for extended periods of time, and PET can be used to measure drug distribution, thus allowing the evaluation of the pharmacokinetics and pharmacodynamics of a particular drug candidate under study. Importantly, PET tracers can be designed and used to quantitate the presence of binding sites in tissues. Consequently, interest in PET tracers for drug development has been expanding based on the development of isotopically labeled biochemicals and appropriate detection devices to detect the radioactivity by external imaging.

Noninvasive nuclear imaging techniques such as PET have been particularly important in providing the ability to study neurological diseases and disorders, including stroke, Parkinson's disease, epilepsy, cerebral tumors and Alzheimer's disease. Alzheimer's disease is the most common form of dementia. It is a neurologic disease characterized by loss of mental ability severe enough to interfere with normal activities of daily living. It usually occurs in old age, and is marked by a decline in cognitive functions such as remembering, reasoning, and planning. All forms of Alzheimer's disease pathology are characterized by the accumulation of amyloid Aβ-peptide. See Cai, L. et al., Current Medicinal Chemistry, 2007, 14, 19-52; Chandra, R. et al. J. Med. Chem. 2007, 50, 2415-2423; Qu, W. et al., J. Med. Chem. 2007, 50, 3380-3387; Cai, L. et al., J. Med. Chem.2007, 50, 4746-4758; and Qu, W. et al., J. Med. Chem. 2007, 50, 2157-2165. PET and single photon emission computed tomography (SPECT), are effective in monitoring the accumulation of amyloid deposits in the brain and correlating it to the progression of AD (Shoghi-Jadid et al. The American Journal of Geriatric Psychiatry 2002, 10, 24; Miller, Science, 2006, 313, 1376; Coimbra et al. Curr. Top. Med. Chem. 2006, 6, 629; Nordberg, Lancet Neurol. 2004, 3, 519). Thus, there is a need for non-toxic amyloid binding radiotracers that can rapidly cross the blood-brain barrier, that have potent, specific binding properties and low non-specific binding properties, that can be used in diagnostics, and that can rapidly clear from the system. These compounds also can be used in monitoring the effectiveness of treatment programs given to Alzheimer's patients by measuring the changes of amyloid plaque level. See Coimbra et al. Curr. Top. Med. Chem. 2006, 6, 629); Mathis et al. J. Med. Chem. 2003, 46, 2740; Klink et al. Ann Neurol. 2004, 55, 306 for background discussion on properties of amyloid binding. See WO 2007/086800, WO2007149030, WO 2007/002540, WO 2007/074786, WO 2002/016333, WO2003048137, WO2002085903, and WO 2004/083195 for examples of compounds and methods used in the treatment of Alzheimer's disease. See also U.S. Pat. No. 6,696,039, US2004/0131545, U.S. Pat. No. 6,001,331, WO2004/032975, WO2004/064869, US2005/0043377, WO2007/033080, U.S. Pat. No.

4,038,396, WO2006044503, WO2006044503, WO2007070173, WO2008108729, WO2008108730, and U.S. Pat. No. 3,899,506.

While the primary use of the isotopically labeled compounds of this invention is in positron emission tomography, which is an in vivo analysis technique, certain of the isotopically labeled compounds can be used for methods other than PET analyses. In particular, $^{14}$C and $^3$H labeled compounds can be used in in vitro and in vivo methods for the determination of binding, receptor occupancy and metabolic studies including covalent labeling. In particular, various isotopically labeled compounds find utility in magnetic resonance imaging, autoradiography and other similar analytical tools.

SUMMARY OF THE INVENTION

The present invention relates to novel amyloid binding compounds and methods for measuring effects of the compounds, by measuring changes of amyloid plaque level in living patients. More specifically, the present invention relates to a method of using the compounds of this invention as tracers in positron emission tomography (PET) imaging to study amyloid deposits in brain in vivo to allow diagnosis of Alzheimer's disease. Thus, the present invention relates to use of the novel amyloid binding compounds as a diagnostic. The invention further relates to a method of measuring clinical efficacy of Alzheimer's disease therapeutic agents. Specifically, the present invention relates to novel aryl or heteroaryl substituted azabenzoxazole derivatives, compositions, and therapeutic uses and processes for making such compounds. The invention is further directed to $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{77}$Br, $^{123}$I, $^{124}$I and $^{131}$I isotopically labeled aryl or heteroaryl substituted azabenzoxazole derivative compounds, compositions, methods of their preparation and their use as PET tracers in diagnosing and measuring the effects of a compound in the treatment of Alzheimer's Disease. The present invention also relates to non-toxic amyloid binding compounds that can rapidly cross the blood brain barrier, have low non-specific binding properties and are rapidly cleared from the system. This and other aspects of the invention will be realized upon review of the specification in its entirety.

DETAILED DESCRIPTION OF THE INVENTION

In one aspect of the invention, there is provided a compound according to formula I:

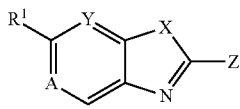

I or a pharmaceutically acceptable salt, solvate or in vivo hydrolysable ester thereof, wherein:
X is O or S;
A and Y independently are N, or CH;
Z is selected from the group consisting of phenyl, benzothiazolyl, indolyl, pyridyl, pyrazolopyridinyl, benzodioxolyl, and pyrrolopyridinyl all optionally substituted with 1 to 3 groups of $R^2$, $R^3$ or $R^4$;
R represents hydrogen, or -$C_{1-6}$alkyl;
$R^1$ represents hydrogen, -$C_{5-10}$ heterocyclyl, —N($R^2$)$_2$, CN, —(CH$_2$)$_n$halo, CF$_3$, —O(CH$_2$)$_n$R, —O(CH$_2$)$_n$C$_{5-10}$heterocyclyl, -$C_{1-6}$alkyl, —OCF$_3$, —O(CH$_2$)$_n$F, —(O(CH$_2$)$_s$)$_p$halo, —(O(CH$_2$)$_s$)$_p$OR, —C(O)OR, or hetero-spirocycle said alkyl, and heterocyclyl optionally substituted with 1 to 3 groups of $R^a$, with the proviso that $R^1$, $R^2$, $R^3$ and $R^4$ are not hydrogen at the same time, or when $R^1$ is hydrogen, Z is phenyl and two of $R^2$, $R^3$ and $R^4$ are hydrogen, then the other of $R^2$, $R^3$ and $R^4$ is not methyl, furyl, halo, hydroxyl, ethoxy, dimethoxy, isopropyloxy, amino, methylamino, dimethylamino or methoxy;
$R^2$, $R^3$ and $R^4$ independently represent hydrogen, —(CH$_2$)$_n$halo, —CF$_3$, —(CH$_2$)$_n$OR, (CH$_2$)$_n$C$_{5-10}$ heterocyclyl, —N(R)$_2$, said alkyl, and heterocyclyl optionally substituted with 1 to 3 groups of $R^a$;
$R^a$ represents —CN, NO$_2$, halo, CF$_3$, -$C_{1-6}$alkyl, -$C_{1-6}$alkenyl, -$C_{1-6}$alkynyl, —(CH$_2$)$_n$halo, —OR, —NRR$^1$, —C(=NR$^1$)NR$^2$R$^3$, —N(=NR$^1$)NR$^2$R$^3$, -NR$^1$COR$^2$, CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$ R$^2$, —COR$^1$, —CO$_2$R$^1$, —CONR$^1$R$^2$, —C(=NR$^1$)R$^2$, or —C(=NOR$^1$)R$^2$;
n represents 0-6;
s represents 2-4; and
p represents 1-3.

One aspect of this invention is realized when $R^2$ is attached to the para position of phenyl, pyridyl and benzothiazolyl of Z, and all other variables are as originally described.

Another aspect of this invention is realized when Z is linked to the azabenzoxazole via its six membered ring and all other variables are as originally described.

Another aspect of this invention is realized when X is O, Y is N and A is CH and all other variables are as originally described.

Another aspect of this invention is realized when X is S, Y is N and A is CH and all other variables are as originally described.

Another aspect of this invention is realized when X is O, Y is CH and A is N and all other variables are as originally described.

Another aspect of this invention is realized when Z is selected from the group consisting of:

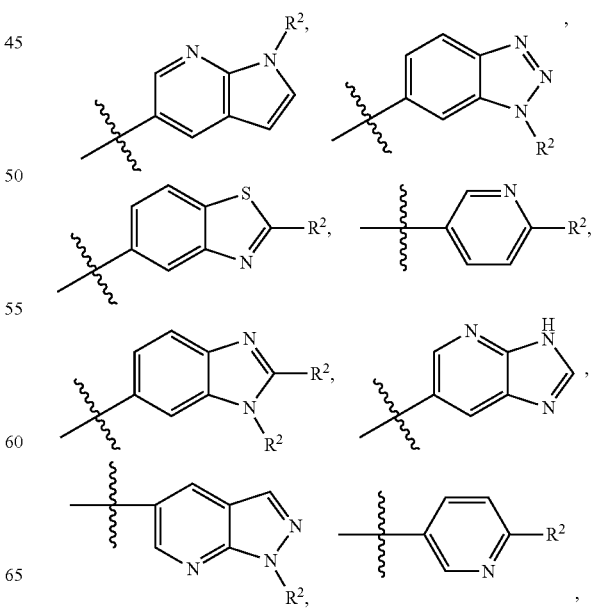

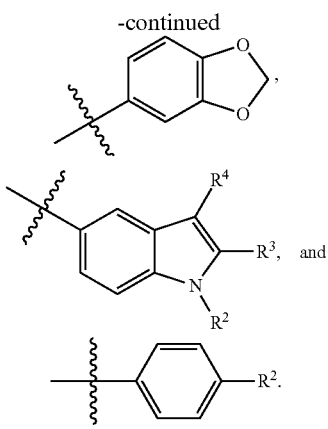

Another aspect of this invention is realized when Z is:

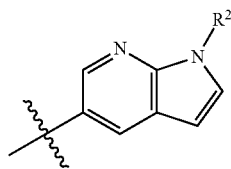

and all other variables are as originally described.

Another aspect of this invention is realized when Z is:

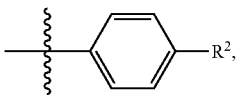

and all other variables are as originally described. A sub-embodiment of this invention is realized when $R^1$ is hydrogen, Z is phenyl and two of $R^2$, $R^3$ and $R^4$ are hydrogen then the other of $R^2$, $R^3$ and $R^4$ is not methyl, furyl, halo, hydroxyl, ethoxy, dimethoxy, isopropyloxy, amino, methylamino, dimethylamino or methoxy.

Still another aspect of this invention is realized when Z is:

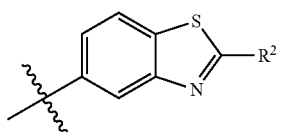

and all other variables are as originally described.

Still another aspect of this invention is realized when Z is:

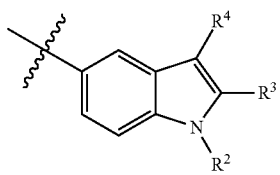

and all other variables are as originally described,

Still another aspect of this invention is realized when Z is:

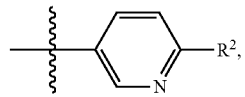

and all other variables are as originally described.

Another aspect of this invention is realized when $R^1$ is selected from the group consisting of -$C_{5-10}$ heterocyclyl, —$N(R^2)_2$, —$(CH_2)_n$halo, —$O(CH_2)_nC_{5-10}$ heterocyclyl, or —$(O(CH_2)_s)_pOR$, —$(O(CH_2)_s)_p$halo, and all other variables are as originally described.

Another aspect of this invention is realized when $R^1$ is selected from the group consisting of halo, -$C_{5-10}$ heterocyclyl, —$N(R^2)_2$, and all other variables are as originally described.

Another aspect of this invention is realized when $R^1$ is fluoro or chloro, preferably fluoro.

Another aspect of this invention is realized when $R^1$ is —$N(R^2)_2$ and all other variables are as originally described. A subembodiment of this invention is realized when $R^2$ is H, $C_{1-6}$ alkyl, —(CH2)nOR, —$(CH_2)_nC_{5-10}$ heterocyclyl.

Another aspect of this invention is realized when $R^1$ is -$C_{5-10}$ heterocyclyl and all other variables are as originally described. A subembodiment of this invention is realized when the heterocyclyl is selected from the group consisting of morpholinyl, furanyl, pyrrolidinyl.

Still another aspect of this invention is realized when $R^2$, $R^3$ and $R^4$ independently represent hydrogen, $C_{1-6}$ alkyl, halo, —$(CH_2)_nOR$, $(CH_2)_nC_{5-10}$ heterocyclyl, $N(R)_2$, said alkyl and heterocyclyl optionally substituted with 1 to 3 groups of $R^a$, and all other variables are as originally described.

Still another aspect of this invention is realized when $R^2$, $R^3$ and $R^4$ independently represent dialkylamino, alkylamino, $C_{1-6}$ alkoxy, $C_{1-6}$ alkyl, all other variables are as originally described.

Yet another aspect of this invention is realized when $R^a$ represents halo, —CN, $NO_2$, -$C_{1-6}$alkyl, —OR, —$N(R)_2$, —$NRCOR^2$, —$NRCO_2R$, or -$C_{5-10}$ heterocyclyl.

Another aspect of the invention is realized when the compounds of formula I are isotopically labeled $^2H$, $^3H$, $^{11}C$, $^{13}C$, $^{14}C$, $^{13}N$, $^{15}N$, $^{15}O$, $^{17}O$, $^{18}O$, $^{18}F$, $^{35}S$, $^{36}CL$, $^{82}Br$, $^{76}Br$, $^{77}Br$, $^{123}I$, $^{124}I$ and $^{131}I$.

Still another aspect of this invention is realized with the compound of structural formula Ia:

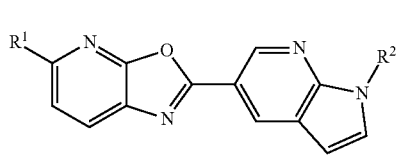

Ia or a pharmaceutically acceptable salt, solvate or in vivo hydrolysable ester thereof, wherein $R^1$, and $R^2$ are as described herein. Another sub-embodiment of formula Ia is realized when $R^1$ is selected from the group consisting of -$C_{5-10}$ heterocyclyl, —$N(R^2)_2$, halo, —$O(CH_2)_nC_{5-10}$ heterocyclyl, —$(O(CH_2)_s)_p$halo, and —$(O(CH_2)_s)_pOR$. Still another embodiment of formula Ia is realized when $R^1$ is halo, -$C_{5-10}$ heterocyclyl, —$N(R^2)_2$. Yet another sub-embodiment of formula Ia is realized when $R^1$ is halo, preferably fluorine.

Still another sub-embodiment of formula Ia is realized when $R^2$ is selected from the group consisting of hydrogen, $C_{1-6}$ alkyl, halo, —$(CH_2)_nOR$, $(CH_2)_nC_{5-10}$ heterocyclyl, and —N(R)$_2$. Another sub-embodiment of formula Ia is realized when R$^2$ is H or C$_{1-6}$ alkyl, preferably C$_{1-6}$ alkyl and still preferably methyl. Still another sub-embodiment of this invention is realized when the compounds of formula Ia are isotopically labeled as $^{11}$C, $^{13}$C, $^{14}$C, $^{18}$F, $^{15}$O, $^{13}$N, $^{35}$S, $^2$H, and $^3$H, preferably $^{11}$C, and $^{18}$F.

Still another aspect of this invention is realized with the compound of structural formula Ib:

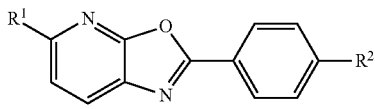

Ib or a pharmaceutically acceptable salt, solvate or in vivo hydrolysable ester thereof, wherein R$^1$, and R$^2$ are as described herein. A sub-embodiment of this is realized provided that when R$^1$ is hydrogen then R$^2$ is not methyl, furyl, halo, hydroxyl, ethoxy, dimethoxy, isopropyloxy, amino, methylamino, dimethylamino or methoxy. A sub-embodiment of formula Ib is realized when R$^1$, and R$^2$ are not hydrogen at the same time. Another sub-embodiment of formula Ib is realized when R$^1$ is selected from the group consisting of -C$_{5-10}$ heterocyclyl, —N(R$^2$)2, halo, —O(CH$_2$)$_n$C$_{5-10}$ heterocyclyl, —(O(CH$_2$)$_s$)$_p$halo, and —(O(CH$_2$)$_s$)$_p$OR. Still another embodiment of formula Ib is realized when R$^1$ is halo, -C$_{5-10}$ heterocyclyl, and —N(R$^2$)$_2$. Yet another sub-embodiment of formula Ib is realized when R$^2$ is selected from the group consisting of —(CH$_2$)$_n$OR, (CH$_2$)$_n$C$_{5-10}$ heterocyclyl, and —N(R)$_2$. Still another sub-embodiment of this invention is realized when the compounds of formula Ib are isotopically labeled as $^{11}$C, $^{13}$C, $^{14}$C, $^{18}$F, $^{15}$O, $^{13}$N, $^{35}$S, $^2$H, and $^3$H, preferably $^{11}$C, and $^{18}$F.

Still another aspect of this invention is realized with the compound of structural formula Ic:

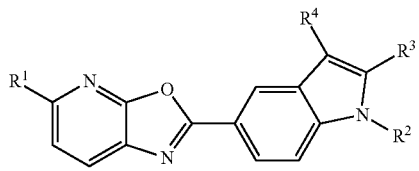

Ic or a pharmaceutically acceptable salt, solvate or in vivo hydrolysable ester thereof, wherein R$^1$, R$^2$, R$^3$ and R$^4$ are as described herein. Another sub-embodiment of formula Ic is realized when R$^1$ is selected from the group consisting of -C$_{5-10}$ heterocyclyl, —N(R$^2$)$_2$, halo, —O(CH$_2$)$_n$C$_{5-10}$ heterocyclyl, —(O(CH$_2$)$_s$)$_p$halo, and —(O(CH$_2$)$_s$)$_p$OR. Still another embodiment of formula Ic is realized when R$^1$ is halo, -C$_{5-10}$ heterocyclyl, —N(R$^2$)$_2$. Yet another sub-embodiment of formula Ic is realized when R$^2$, R$^3$ and R$^4$ are independently selected from the group consisting of hydrogen, C$_{1-6}$ alkyl, halo, —(CH$_2$)$_n$OR, (CH$_2$)$_n$C$_{5-10}$ heterocyclyl, and —N(R)$_2$. Still another sub-embodiment of this invention is realized when the compounds of formula Ic are isotopically labeled as $^{11}$C, $^{13}$C, $^{14}$C, $^{18}$F, $^{15}$O, $^{13}$N, $^{35}$S, $^2$H, and $^3$H, preferably, $^{11}$C, and $^{18}$F.

Examples of compounds of this invention are:

| Structure | Nomenclature | M + 1 |
|---|---|---|
| 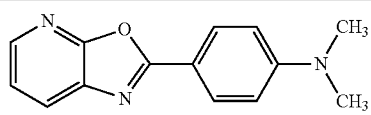 | [3H]-N,N-dimethyl-4-[1,3]oxazolo[5,4-b]-pyridin-2-ylaniline | 246 |
| 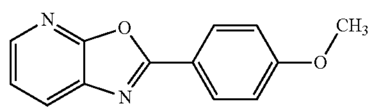 [SMILES: COc1ccc(-c2nc3cccnc3o2)cc1] | 2-(4-methoxyphenyl)[1,3]oxazolo[5,4-b]pyridine | 227 |
| 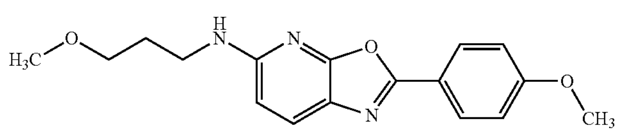 | 2-(4-methoxyphenyl)-N-(3-methoxypropyl)[1,3]oxazolo[5,4-b]pyridin-5-amine | 314 |
| 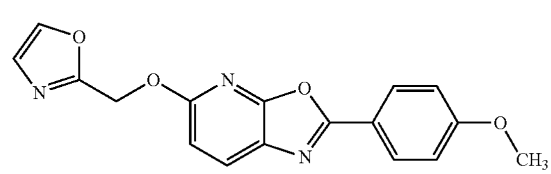 [SMILES: COc1ccc(-c2nc3ccc(OCc4ncco4)nc3o2)cc1] | 2-(4-methoxyphenyl)-5-(1,3-oxazol-2-ylmethoxy)[1,3]oxazolo[5,4-b]pyridine | 324 |
| 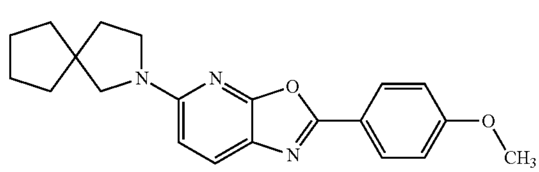 | 5-(2-azaspiro[4.4]non-2-yl)-2-(4-methoxyphenyl)[1,3]oxazolo[5,4-b]pyridine | 350 |

-continued

| Structure | Nomenclature | M + 1 |
|---|---|---|
| 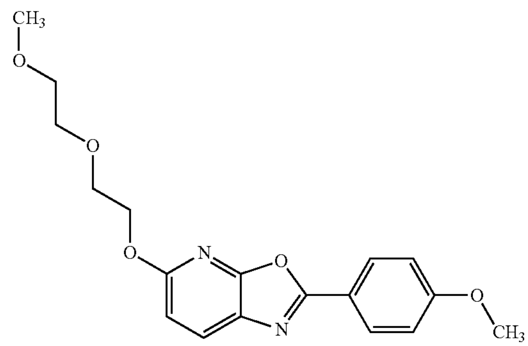 [SMILES: COCCOCCOc1ccc2nc(-c3ccc(OC)cc3)oc2n1] | 5-[2-(2-methoxyethoxy)ethoxy]-2-(4-methoxyphenyl)[1,3]oxazolo[5,4-b]pyridine | 345 |
| 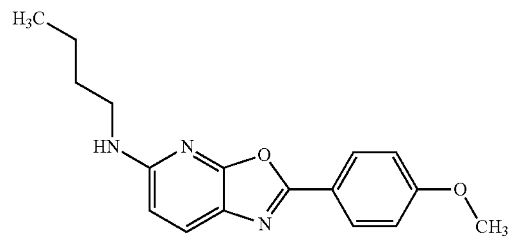 [SMILES: CCCCNc1ccc2nc(-c3ccc(OC)cc3)oc2n1] | N-butyl-2-(4-methoxyphenyl)[1,3]oxazolo[5,4-b]pyridin-5-amine | 298 |
| 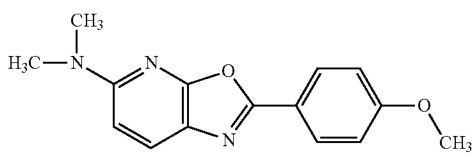 | 2-(4-methoxyphenyl)-N,N-dimethyl[1,3]oxazolo[5,4-b]pyridin-5-amine | 270 |
| 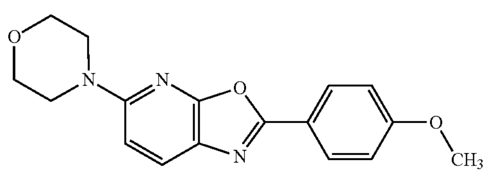 [SMILES: COc1ccc(-c2nc3ccc(N4CCOCC4)nc3o2)cc1] | 2-(4-methoxyphenyl)-5-morpholin-4-yl[1,3]oxazolo[5,4-b]pyridine | 312 |
| 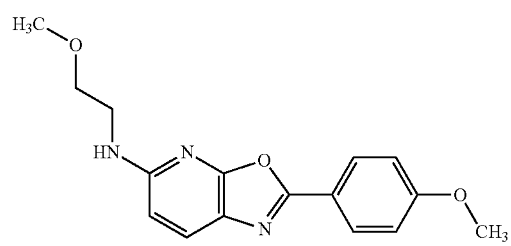 | N-(2-methoxyethyl)-2-(4-methoxyphenyl)[1,3]oxazolo[5,4-b]pyridin-5-amine | 300 |
| 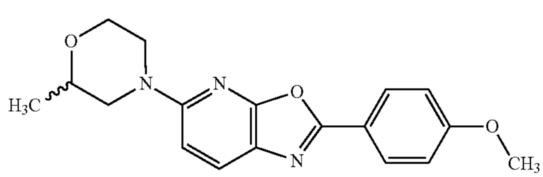 | 2-(4-methoxyphenyl)-5-(2-methylmorpholin-4-yl)[1,3]oxazolo[5,4-b]pyridine | 326 |
| 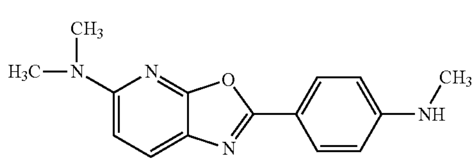 | N,N-dimethyl-2-[4-(methylamino)phenyl][1,3]oxazolo[5,4-b]pyridin-5-amine | 269 |

-continued

| Structure | Nomenclature | M + 1 |
|---|---|---|
| 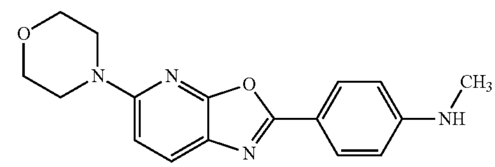 [SMILES: CNc1ccc(-c2nc3ccc(N4CCOCC4)nc3o2)cc1] | N-methyl-4-(5-morpholin-4-yl[1,3]oxazolo[5,4-b]pyridin-2-yl)aniline | 311 |
| 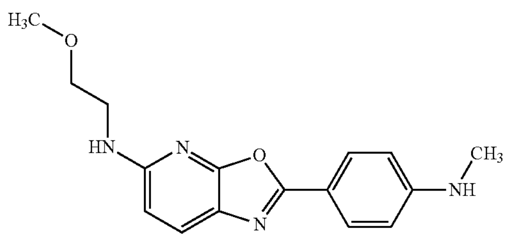 | N-(2-methoxyethyl)-2-[4-(methylamino)phenyl][1,3]oxazolo[5,4-b]pyridin-5-amine | 299 |
| | N-methyl-4-[5-(2-methylmorpholin-4-yl)[1,3]oxazolo[5,4-b]pyridin-2-yl]aniline | 325 |
| 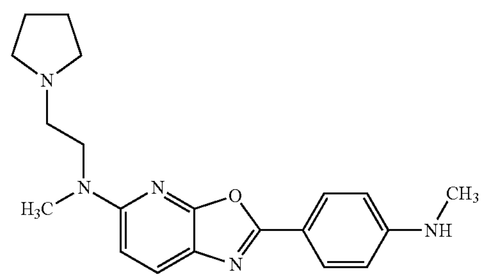 [SMILES: CNc1ccc(-c2nc3ccc(N(C)CCN4CCCC4)nc3o2)cc1] | N-methyl-2-[4-(methylamino)phenyl]-N-(2-pyrrolidin-1-ylethyl)[1,3]oxazolo[5,4-b]pyridin-5-amine | 352 |
| 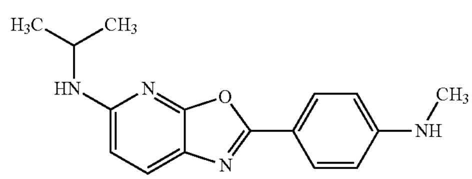 [SMILES: CNc1ccc(-c2nc3ccc(NC(C)C)nc3o2)cc1] | 2-[4-(methylamino)phenyl]-N-(1-methylethyl)[1,3]oxazolo[5,4-b]pyridin-5-amine | 283 |
| 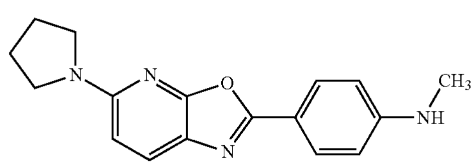 [SMILES: CNc1ccc(-c2nc3ccc(N4CCCC4)nc3o2)cc1] | N-methyl-4-(5-pyrrolidin-1-yl[1,3]oxazolo[5,4-b]pyridin-2-yl)aniline | 295 |
| 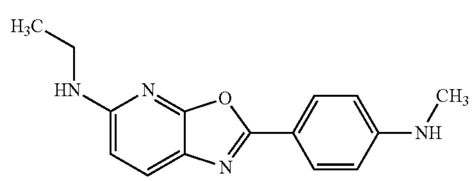 [SMILES: CCNc1ccc2nc(-c3ccc(NC)cc3)oc2n1] | N-ethyl-2-[4-(methylamino)phenyl][1,3]oxazolo[5,4-b]pyridin-5-amine | 269 |
| 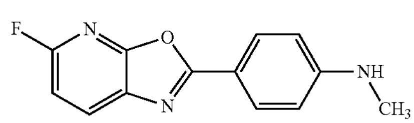 | 4-(5-fluoro[1,3]oxazolo[5,4-b]pyridin-2-yl)-N-methylaniline | 244 |

-continued

| Structure | Nomenclature | M + 1 |
|---|---|---|
| 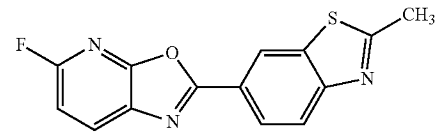 [SMILES: Cc1nc2ccc(-c3nc4ccc(F)nc4o3)cc2s1] | 5-fluoro-2-(2-methyl-1,3-benzothiazol-6-yl)[1,3]oxazolo[5,4-b]pyridine | 286 |
| 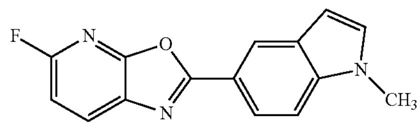 [SMILES: Cn1ccc2cc(-c3nc4ccc(F)nc4o3)ccc21] | 5-fluoro-2-(1-methyl-1H-indol-5-yl)[1,3]oxazolo[5,4-b]pyridine | 268 |
| 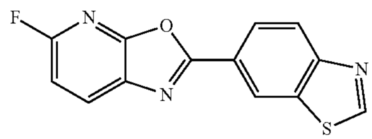 [SMILES: Fc1ccc2nc(-c3ccc4ncsc4c3)oc2n1] | 2-(1,3-benzothiazol-6-yl)-5-fluoro[1,3]oxazolo[5,4-b]pyridine | 272 |
| 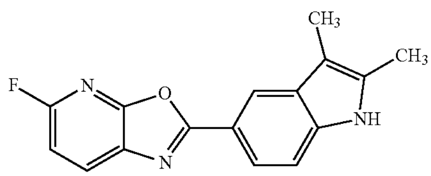 [SMILES: Cc1[nH]c2ccc(-c3nc4ccc(F)nc4o3)cc2c1C] | 2-(2,3-dimethyl-1H-indol-5-yl)-5-fluoro[1,3]oxazolo[5,4-b]pyridine | 282 |
| | 5-fluoro-2-(6-fluoro-5-methylpyridin-3-yl)[1,3]oxazolo[5,4-b]pyridine | 248 |
| 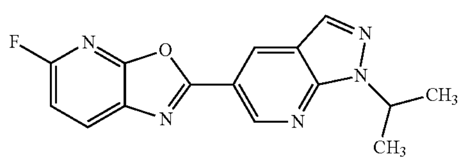 [SMILES: CC(C)n1ncc2cc(-c3nc4ccc(F)nc4o3)cnc21] | 5-fluoro-2-[1-(1-methylethyl)-1H-pyrazolo[3,4-b]pyridin-5-yl][1,3]oxazolo[5,4-b]pyridine | 298 |
| 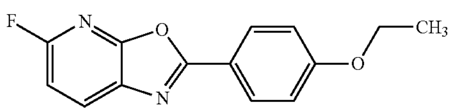 [SMILES: CCOc1ccc(-c2nc3ccc(F)nc3o2)cc1] | 2-(4-ethoxyphenyl)-5-fluoro[1,3]oxazolo[5,4-b]pyridine | 259 |
| 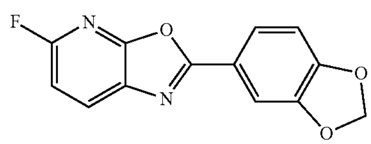 [SMILES: Fc1ccc2nc(-c3ccc4c(c3)OCO4)oc2n1] | 2-(1,3-benzodioxol-5-yl)-5-fluoro[1,3]oxazolo[5,4-b]pyridine | 259 |
| 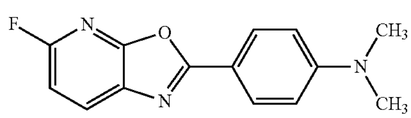 | 4-(5-fluoro[1,3]oxazolo[5,4-b]pyridin-2-yl)-N,N-dimethylaniline | 258 |
| 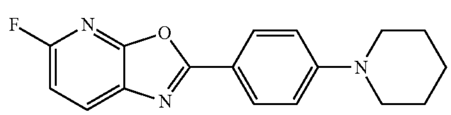 [SMILES: Fc1ccc2nc(-c3ccc(N4CCCCC4)cc3)oc2n1] | 5-fluoro-2-(4-piperidin-1-ylphenyl)[1,3]oxazolo[5,4-b]pyridine | 298 |
| 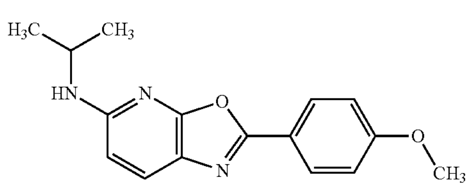 | 2-(4-methoxyphenyl)-N-(1-methylethyl)[1,3]oxazolo[5,4-b]pyridin-5-amine | 284 |

-continued

| Structure | Nomenclature | M + 1 |
|---|---|---|
| 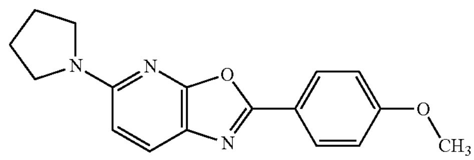 | 2-(4-methoxyphenyl)-5-pyrrolidin-1-yl[1,3]oxazolo[5,4-b]pyridine | 296 |
| 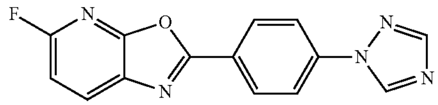 [SMILES: Fc1ccc2nc(-c3ccc(-n4cncn4)cc3)oc2n1] | 5-fluoro-2-[4-(1H-1,2,4-triazol-1-yl)phenyl][1,3]oxazolo[5,4-b]pyridine | 282 |
| 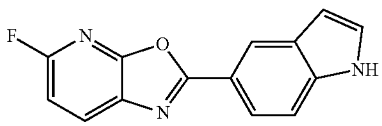 [SMILES: Fc1ccc2nc(-c3ccc4[nH]ccc4c3)oc2n1] | 5-fluoro-2-(1H-indol-5-yl)[1,3]oxazolo[5,4-b]pyridine | 254 |
| 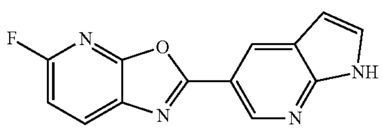 [SMILES: Fc1ccc2nc(-c3cnc4[nH]ccc4c3)oc2n1] | 5-fluoro-2-(1H-pyrrolo[2,3-b]pyridin-5-yl)[1,3]oxazolo[5,4-b]pyridine | 255 |
| 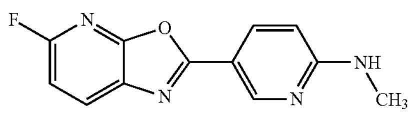 | [5-(5-Fluoro-oxazolo[5,4-b]pyridin-2-yl)-pyridin-2-yl]-methyl-amine | 245 |
| 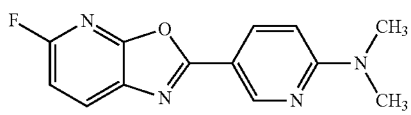 | [5-(5-Fluoro-oxazolo[5,4-b]pyridin-2-yl)-pyridin-2-yl]-dimethyl-amine | 259 |
| 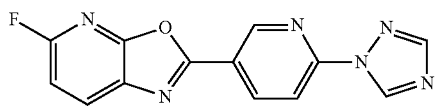 [SMILES: Fc1ccc2nc(-c3ccc(-n4cncn4)nc3)oc2n1] | 5-Fluoro-2-(6-[1,2,4]triazol-1-yl-pyridin-3-yl)-oxazolo[5,4-b]pyridine | 283 |
| 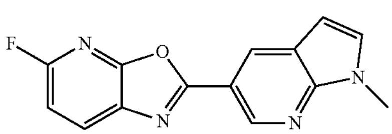 [SMILES: Cn1ccc2cc(-c3nc4ccc(F)nc4o3)cnc21] | 5-Fluoro-2-(1-methyl-1H-pyrrolo[2,3-b]pyridin-5-yl)-oxazolo[5,4-b]pyridine | 269 |
| 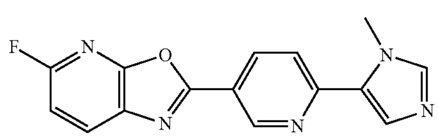 [SMILES: Cn1cncc1-c1ccc(-c2nc3ccc(F)nc3o2)cn1] | 5-Fluoro-2-[6-(3-methyl-3H-imidazol-4-yl)-pyridin-3-yl]-oxazolo[5,4-b]pyridine | 296 |
| 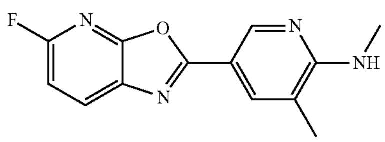 [SMILES: CNc1ncc(-c2nc3ccc(F)nc3o2)cc1C] | [5-(5-Fluoro-oxazolo[5,4-b]pyridin-2-yl)-3-methyl-pyridin-2-yl]-methyl-amine | 259 |
| | 5-Fluoro-2-(1-methyl-1H-indazol-5-yl)-oxazolo[5,4-b]-pyridine | 269 |

| Structure | Nomenclature | M + 1 |
|---|---|---|
| 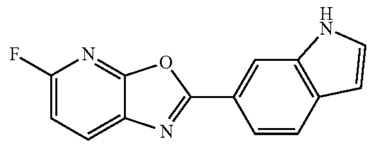 [SMILES: Fc1ccc2nc(-c3ccc4cc[nH]c4c3)oc2n1] | 5-Fluoro-2-(1H-indol-6-yl)-oxazolo[5,4-b]pyridine | 254 |
| 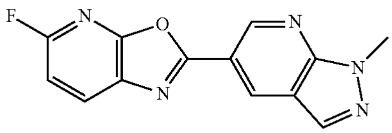 [SMILES: Cn1ncc2cc(-c3nc4ccc(F)nc4o3)cnc21] | 5-Fluoro-2-(1-methyl-1H-pyrazolo[3,4-b]pyridin-5-yl)-oxazolo[5,4-b]pyridine | 270 |
| 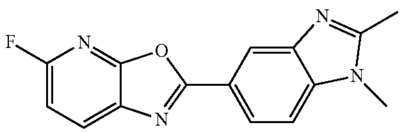 [SMILES: Cc1nc2cc(-c3nc4ccc(F)nc4o3)ccc2n1C] | 2-(1,2-Dimethyl-1H-benzoimidazol-5-yl)-5-fluoro-oxazolo[5,4-b]pyridine | 283 |
| 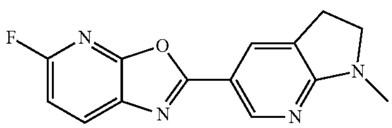 [SMILES: CN1CCc2cc(-c3nc4ccc(F)nc4o3)cnc21] | 5-Fluoro-2-(1-methyl-2,3-dihydro-1H-pyrrolo[2,3-b]pyridin-5-yl)-oxazolo[5,4-b]pyridine | 271 |
| 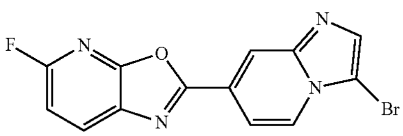 [SMILES: Fc1ccc2nc(-c3ccn4c(Br)cnc4c3)oc2n1] | 2-(3-Bromo-imidazo[1,2-a]pyridin-7-yl)-5-fluoro-oxazolo[5,4-b]pyridine | 333 |
| 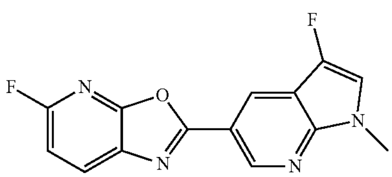 [SMILES: Cn1cc(F)c2cc(-c3nc4ccc(F)nc4o3)cnc21] | 5-Fluoro-2-(3-fluoro-1-methyl-1H-pyrrolo[2,3-b]pyridin-5-yl)-oxazolo[5,4-b]pyridine | 287 |
| 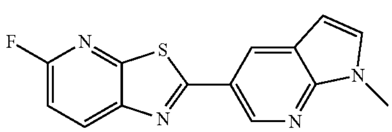 [SMILES: Cn1ccc2cc(-c3nc4ccc(F)nc4s3)cnc21] | 5-Fluoro-2-(1-methyl-1H-pyrrolo[2,3-b]pyridin-5-yl)-thiazolo[5,4-b]pyridine | |
| 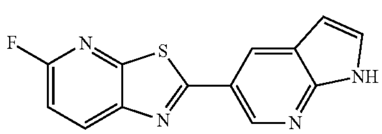 | 5-Fluoro-2-(1H-pyrrolo[2,3-b]pyridin-5-yl)-thiazolo[5,4-b]pyridine | |
| | [4-(6-Fluoro-oxazolo[4,5-c]pyridin-2-yl)-phenyl]-dimethyl-amine | | or a pharmaceutically acceptable salt, solvate or in vivo hydrolysable ester thereof.

Further examples of the compounds of this invention are:
[5-(5-Fluoro-oxazolo[5,4-b]pyridin-2-yl)-pyridin-2-yl]-methyl-amine,
[5-(5-Fluoro-oxazolo[5,4-b]pyridin-2-yl)-pyridin-2-yl]-dimethyl-amine,
4-(5-fluoro[1,3]oxazolo[5,4-b]pyridin-2-yl)-N-methylaniline,
4-(5-fluoro[1,3]oxazolo[5,4-b]pyridin-2-yl)-N,N-dimethylaniline,
5-fluoro-2-(1H-indol-5-yl)[1,3]oxazolo[5,4-b]pyridine;
5-fluoro-2-(1H-pyrrolo[2,3-b]pyridin-5-yl)[1,3]oxazolo[5,4-b]pyridine;
or a pharmaceutically acceptable salt, solvate or in vivo hydrolysable ester thereof.

The present invention also relates to methods for measuring effects of the compounds, by measuring changes of amyloid plaque level in living patients. More specifically, the present invention relates to a method of using the compounds of this invention as tracers in positron emission tomography (PET) imaging to study amyloid deposits in brain in vivo to allow diagnosis of Alzheimer's disease. Thus, the present invention relates to use of the novel amyloid binding compounds as a diagnostic. The invention further relates to the use of the novel amyloid binding compounds in the manufacture of a medicament for treating Alzheimer's disease. The invention further relates to a method of measuring clinical efficacy of Alzheimer's disease therapeutic agents. Specifically, the present invention relates to novel aryl or heteroaryl substituted azabenzoxazole derivatives, compositions, and therapeutic uses and processes for making such compounds. The invention is further directed to $^{2}$H, $^{3}$H, $^{11}$C, $^{13}$C, $^{14}$C, $^{13}$N, $^{15}$N, $^{15}$O, $^{17}$O, $^{18}$O, $^{18}$F, $^{35}$S, $^{36}$CL, $^{82}$B$_r$, $^{76}$Br, $^{77}$Br, $^{123}$I, $^{124}$I and $^{131}$I, preferably $^{11}$C, $^{13}$C, $^{14}$C, $^{18}$F, $^{15}$O, $^{13}$N, $^{35}$S, $^{2}$H, and $^{3}$H, more preferably $^{11}$C, and $^{18}$F isotopically labeled aryl or heteroaryl substituted azabenzoxazole derivative compounds, compositions and methods of their preparation. The present invention also relates to non-toxic amyloid binding compounds that can rapidly cross the blood brain barrier, have low non-specific binding properties and rapidly clear from the system.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

When any variable (e.g. aryl, heterocycle, $R^{1a}$, $R^{6}$ etc.) occurs more than one time in any constituent, its definition on each occurrence is independent at every other occurrence. Also, combinations of substituents/or variables are permissible only if such combinations result in stable compounds.

In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

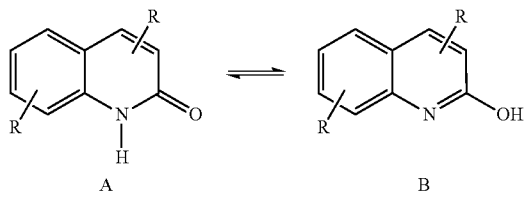

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is $C_2$-$C_6$ alkenyl.
Preferably, alkynyl is $C_2$-$C_6$ alkynyl.

As used herein, "cycloalkyl" is intended to include cyclic saturated aliphatic hydrocarbon groups having the specified number of carbon atoms. Preferably, cycloalkyl is $C_3$-$C_{10}$ cycloalkyl. Examples of such cycloalkyl elements include, but are not limited to, cyclopropyl, cyclobutyl, cyclopentyl, cyclohexyl and cycloheptyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The tem heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyly, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

Preferably, heterocycle is selected from 2-azepinonyl, benzimidazolyl, 2-diazapinonyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroaryl-sulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1-C_6$ alkyl$)_2$, $NO_2$, CN, $(C_1-C_6$ alkyl)O—, (aryl)O—, —OH, $(C_1-C_{6\ 1\ alkyl)S(O)m}$—, $(C_1-C_6$ alkyl)C(O)NH—, $H_2N$—C(NH)—, $(C_1-C_6$ alkyl)C(O)—, $(C_1-C_6$ alkyl)OC(O)—, $(C_1-C_6$ alkyl)OC(O)NH—, phenyl, pyridyl, imidazolyl, oxazolyl, isoxazolyl, thiazolyl, thienyl, furyl, isothiazolyl and $C_1-C_{20}$ alkyl.

As used herein, "in vivo hydrolysable precursors" means an in vivo hydrolysable (or cleavable) ester of a compound of formula I that contains a carboxy or a hydroxy group. For example amino acid esters, C1-6 alkoxymethyl esters like methoxymethyl; $C_{1-6}$ alkanoyloxymethyl esters like pivaloyloxymethyl; $C_{3-8}$ cycloalkoxycarbonyloxy, $C_{1-6}$ alkyl esters like 1-cyclohexylcarbonyloxyethyl, acetoxymethoxy, or phosphoramidic cyclic esters.

Examples of an "effective amount" include amounts that enable imaging of amyloid deposit(s) in vivo, that yield acceptable toxicity and bioavailability levels for pharmaceutical use, and/or prevent cell degeneration and toxicity associated with fibril formation.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sei.*, 1977:66:1-19.

As indicated herein the present invention includes isotopically labeled compounds of the invention. An "isotopically-labeled", "radio-labeled", "tracer", "labeled tracer" "radioligand" or "detectable amyloid binding" compound, is a compound where one or more atoms are replaced or substituted by an atom having an atomic mass or mass number different from the atomic mass or mass number typically found in nature (i.e., naturally occurring). Suitable radionuclides (i.e. "detectable isotopes") that may be incorporated in compounds of the present invention include but are not limited to $^2H$, $^3H$, $^{11}C$, $^{13}C$, $^{14}C$, $^{13}N$, $^{15}N$, $^{15}O$, $^{17}O$, $^{18}O$, $^{18}F$, $^{35}S$, $^{36}O$, $^{82}Br$, $^{76}Br$, $^{77}Br$, $^{123}I$, $^{124}I$ and $^{131}I$. The isotopically labeled compounds of the invention need only to be enriched with a detectable isotope to, or above, the degree which allows detection with a technique suitable for the particular application. The radionuclide that is incorporated in the instant radiolabeled compounds will depend on the specific application of that radiolabeled compound. In another embodiment of the invention the radionuclides are represented by $^{11}C$, $^{13}C$, $^{14}C$, $^{18}F$, $^{15}O$, $^{13}N$, $^{35}S$, $^2H$, and $^3H$, preferably $^{11}C$, and $^{18}F$.

This invention further relates to a pharmaceutical composition comprising an effective amount of at least one compound of formula I and a pharmaceutically acceptable carrier. The composition may comprise, but is not limited to, one or more buffering agents, wetting agents, emulsifiers, suspending agents, lubricants, adsorbents, surfactants, preservatives and the like. The composition may be formulated as a solid, liquid, gel or suspension for oral administration (e.g., drench, bolus, tablet, powder, capsule, mouth spray, emulsion); parenteral administration (e.g., subcutaneous, intramuscular, intravenous, epidural injection); topical application (e.g., cream, ointment, controlled-released patch, spray); intravaginal, intrarectal, transdermal, ocular, or nasal administration.

This invention provides radiolabeled aryl or heteroaryl substituted azabenzoxazole derivatives as amyloid imaging agents and synthetic precursor compounds from which they are prepared. The compounds formula I are active against age-related diseases such as Alzheimer, as well as other pathologies such as Downs syndrome and beta-amyloid angiopathy. The compounds of this invention may also be used in combination with a broad range of cognition deficit enhancement agents. Thus, in another embodiment of this invention a compound of formula (I) or a pharmaceutically acceptable salt, solvate or in vivo hydrolysable ester thereof, or a pharmaceutical composition or formulation comprising a compound of formula (I) is administered concurrently, simultaneously, sequentially or separately with another pharmaceutically active compound or compounds used in Alzheimer's therapies including for example donepezil, memantine, tacrine and equivalents and pharmaceutically active isomer(s) and metabolite(s) thereof.

This invention further relates to a method of treating or preventing an Aβ-related pathology in a patient comprising administering a therapeutically effective amount of a compound of formula I. This invention also provides a method for treating neurodegenerative disorders such as dementia, Cognitive Deficit in Schizophrenia, Mild Cognitive Impairment, Age Associated Memory Impairment, Age-Related Cognitive Decline, and the like.

An ultimate objective of the present invention is to provide a radiopharmaceutical agent, useful in PET imaging that has high specific radioactivity and high target tissue selectivity by virtue of its high affinity for amyloid plaques. The tissue selectivity is capable of further enhancement by coupling this highly selective radiopharmaceutical with targeting agents, such as microparticles.

In another aspect of this invention the claimed compounds have an unexpectedly low binding potential in amyloid free cortical gray matter and adjacent white matter, which provides improved profiles with regard to binding potential in white matter.

In accordance with the present invention, the most preferred method for imaging beta-amyloid plaque in a patient, wherein an isotopically labeled novel aryl or heteroaryl substituted azabenzoxazole derivative is employed as the imaging agent, comprises the following steps: the patient is placed in a supine position in the PET camera, and a sufficient amount (<10 mCi) of an isotopically labeled aryl or heteroaryl substituted azabenzoxazole derivative is administered to the brain tissue of the patient. An emission scan of the cerebral region is performed. The technique for performing an emission scan of the head is well known to those of skilled in the art. PET techniques are described in Freeman et al., Freeman and Johnson's Clinical Radionuclide Imaging. 3rd. Ed. Vol. 1 (1984); Grune & Stratton, New York; Ennis et Q. Vascular Radionuclide Imaging: A Clinical Atlas, John Wiley & Sons, New York (1983).

The term "labeled tracer" refers to any molecule which can be used to follow or detect a defined activity in viva, for example, a preferred tracer is one that accumulates in the regions where beta-amyloid plaque may be found. Preferably, the labeled tracer is one that can be viewed in a living experimental animal, healthy human or patient (referred to as a subject), for example, by positron emission tomograph (PET) scanning. Suitable labels include, but are not limited to radioisotopes, fluorochromes, chemiluminescent compounds, dyes, and proteins, including enzymes.

The present invention also provides methods of determining in vivo activity of an enzyme or other molecule. More specifically, a tracer, which specifically tracks the targeted activity, is selected and labeled. In a preferred embodiment, the tracer tracks binding activity of amyloid Aβ-peptide in the brain and central nervous system. The tracer provides the means to evaluate various neuronal processes, including fast excitatory synaptic transmission, regulation of neurotransmitter release, and long-term potentiation. The present invention gives researchers the means to study the biochemical mechanisms of pain, anxiety/depression, drug addiction and withdrawal, disorders of the basal ganglia, eating disorders, obesity, long-term depression, learning and memory, developmental synaptic plasticity, hypoxic-ischemic damage and neuronal cell death, epileptic seizures, visual processing, as well as the pathogenesis of several neurodegenerative disorders.

Biomarkers of Alzheimer's disease state, prognosis and progression will all be useful for general diagnostic utilities as well as for clinical development plans for therapeutic agents for Alzheimer's disease. The present invention will provide biomarker information as patients are enrolled in clinical trials for new Alzheimer's treatments to assist in patient selection and assignment to cohorts. The present invention will serve as one of the biomarkers of disease state in order to get the correct patients into the proper PhIIb trial cohort. In addition, the present invention can serve as one marker of disease prognosis as an entry inclusion criterion in order to enhance the probability that the disease will progress in the placebo treatment arm, an issue that has plagued recent AD clinical trials. Finally, the present invention can serve as one biomarker of disease progression to monitor the clinical course of patients on therapy and could provide an independent biomarker measure of treatment response by a therapeutic drug.

Compounds within this invention are inhibitors and/or binders of monoamineoxidase B (MAO-B). Compounds, and isotopically labeled variants thereof, may be useful for the diagnosis and/or treatment of Alzheimer's disease, depression, schizophrenia, or Parkinson's disease. Means of detecting labels are well known to those skilled in the art. For example, isotopic labels may be detected using imaging techniques, photographic film or scintillation counters. In a preferred embodiment, the label is detected in vivo in the brain of the subject by imaging techniques, for example positron emission tomography (PET).

The labeled compound of the invention preferably contains at least one radionuclide as a label. Positron-emitting radionuclides are all candidates for usage. In the context of this invention the radionuclide is preferably selected from $^{11}C$, $^{13}C$, $^{14}C$, $^{18}F$, $^{15}O$, $^{13}N$, $^{35}S$, $^{2}H$, and $^{3}H$, more preferably from $^{11}C$, and $^{18}F$.

The tracer can be selected in accordance with the detection method chosen. Before conducting the method of the present invention, a diagnostically effective amount of a labeled or unlabeled compound of the invention is administered to a living body, including a human.

The diagnostically effective amount of the labeled or unlabeled compound of the invention to be administered before conducting the in-vivo method for the present invention is within a range of from 0.1 ng to 100 mg per kg body weight, preferably within a range of from 1 ng to 10 mg per kg body weight.

In accordance with another embodiment of the present invention, there are provided methods for the preparation of heterocyclic compounds as described above. For example, the heterocyclic compounds described above can be prepared using synthetic chemistry techniques well known in the art (see *Comprehensive Heterocyclic Chemistry*, Katritzky, A. R. and Rees, C. W. eds., Pergamon Press, Oxford, 1984) from a precursor of the substituted heterocycle of Formula 1 as outlined below. The isotopically labeled compounds of this invention are prepared by incorporating an isotope such as $^{11}C$, $^{13}C$, $^{14}C$, $^{18}F$, $^{15}O$, $^{13}N$, $^{35}S$, $^{2}H$, and $^{3}H$ into the substrate molecule. This is accomplished by utilizing reagents that have had one or more of the atoms contained therein made radioactive by placing them in a source of radioactivity such as a nuclear reactor, a cyclotron and the like. Additionally many isotopically labeled reagents, such as $^{2}H_2O$, $^{3}H_3Cl$, $^{14}C_6H_5Br$, $ClCH_2^{14}COCl$ and the like, are commercially available. The isotopically labeled reagents are then used in standard organic chemistry synthetic techniques to incorporate the isotope atom, or atoms, into a compound of Formula I as described below. The following Schemes illustrate how to make the compounds of formula I.

Abbreviations used in the description of the chemistry and in the Examples that follow are:

| | |
|---|---|
| CH$_2$Cl$_2$ | dichloromethane |
| Boc | tert-butoxycarbonyl |
| DIEA | diisopropylethylamine |
| PMB | 4-methoxy-benzyl |
| PMBBr | 4-methoxy-benzyl bromide |
| THF | tetrahydrofuran |
| TFA | trifluoroacteic acid |
| MeOH | methanol |
| PS-PPh3 | polystyrene triphenyphosphine |
| DMF | N,N-dimethylformamide |
| DMA | N,N-dimethylacetamide |
| EtOAc | ethyl acetate |
| AD | Alzheimer's Disease |
| NMR | Nuclear Magnetic Resonance |
| DMSO | dimethyl sulfoxide |

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

General Reaction Scheme 1

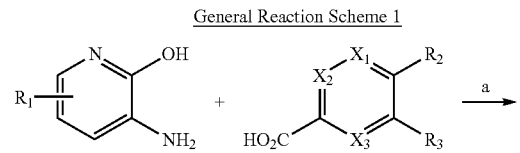

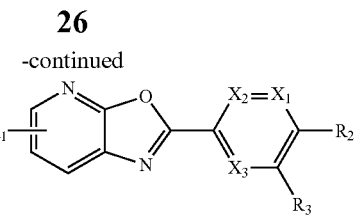

X$_{1-3}$ = independently N or CH
a) R$_2$CO$_2$H, PS—PPh$_3$, CCl$_3$CN, heat;

As illustrated in General Reaction Scheme 1, a suitably substituted 3-amino-2-pyridone is reacted with a suitably substituted carboxylic acid in the presence of trichloroacetonitrile and polystyrene supported triphenylphosphine to provide the corresponding 7-aza-benzoxazole. In situations where the carboxylic acid portion of the molecule contains a Boc or PMB protecting group, it can then be subsequently removed upon reaction with trifluoroacetic acid to afford the final material. In this instance, all carboxylic acids and 3-amino-2-pyridones were commercially available.

Scheme 1

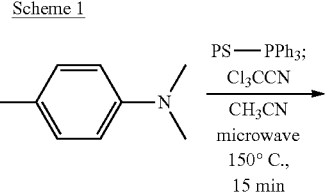

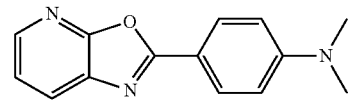

EXAMPLE 1

Dimethyl-(4-oxazolo[5,4-b]pyridin-2-yl-phenyl)-amine

3-Amino-pyridin-2-ol (50 mg, 0.45 mmol), 4-dimethylamino-benzoic acid (74 mg, 0.45 mmol), trichloroacetonitrile (91 μL, 0.91 mmol), and polystyrene triphenylphosphine (425 mg, 1.362 mmol) were suspended in acetonitrile (4.5 mL) and heated by microwave to 150° C. for 15 min. The crude reaction mixture was filtered and concentrated affording a residue which was purified by reverse phase chromatography affording dimethyl-(4-oxazolo[5,4-b]pyridin-2-yl-phenyl)-amine (7.1 mg, 0.030 mmol, 6.6% yield). ES MS (M+H$^+$)=240; $^1$H NMR (300 MHz, CDCl$_3$): δ 8.24 (d, J=5.1 Hz, 1H); 8.14 (d, J=8.6 Hz, 2H); 7.95 (d, J=7.8 Hz, 1H); 7.28 (dd, J=7.7, 4.9 Hz, 2H); 6.78 (d, J=8.6 Hz, 1H); 3.09 (s, 6H); HRMS m/z 240.1122 (C$_{14}$H$_{13}$N$_3$O$_1$+H$^+$ requires 240.1132).

General Reaction Scheme 2

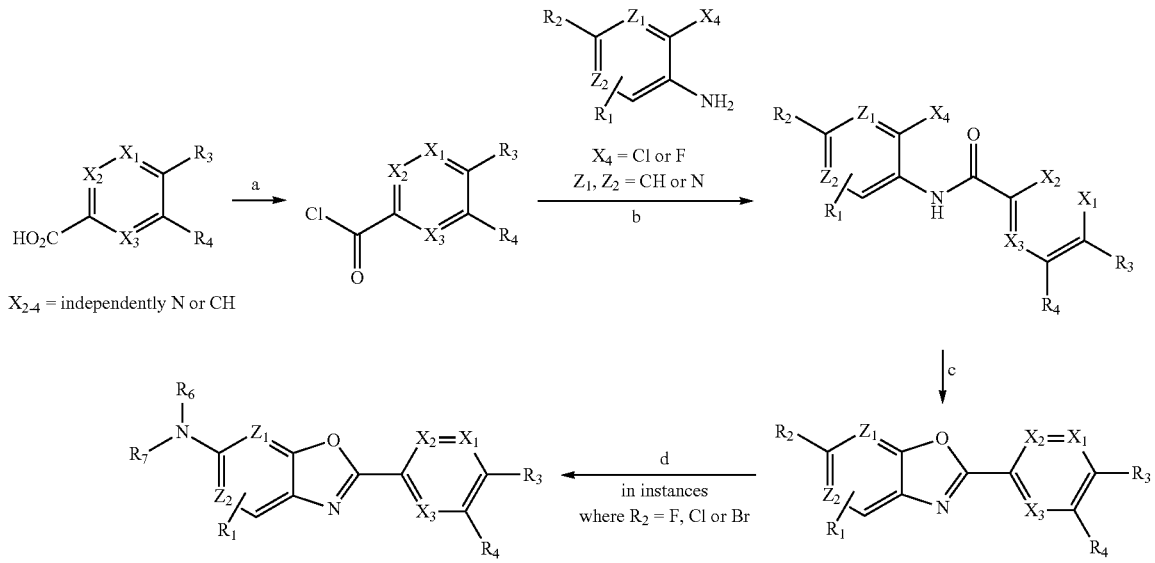

a) 1-Chloro-N,N-2-trimethyl-1-propenylamine or (COCl)$_2$, cat. DMF; b) pyridine; c) Cs$_2$CO$_3$ or K$_2$CO$_3$, heat; d) R$_6$R$_7$NH, Cs$_2$CO$_3$ or Pd cat., R$_6$R$_7$NH As illustrated in General Reaction Scheme 2, suitably substituted carboxylic acids can be reacted with 1-chloro-N,N-2-trimethyl-1-propenylamine or oxalyl chloride and catalytic DMF to generate acid chlorides which in turn are reacted with suitably substituted 2-halo-3-amino pyridines to provide the corresponding amides, which are then converted into the corresponding 7-azabenzoxazoles or 4-azabenzoxazoles upon reaction with K$_2$CO$_3$ or Cs$_2$CO$_3$ at elevated temperature. In some instances, the carboxylic acid starting material may contain a Boc or PMB protecting group, which may be subsequently removed upon reaction with trifluoroacetic acid and/or heating to afford the final material. In this instance, all carboxylic acids, 2-amino-phenols, and 3-amino-2-pyridones were commercially available or were prepared using procedures known to those skilled in the art.

Scheme 2

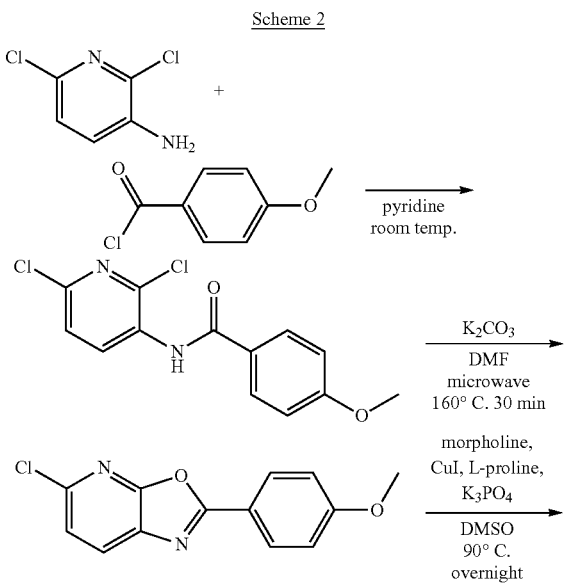

-continued

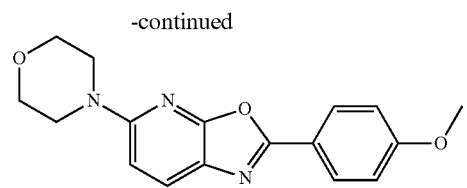

EXAMPLE 2

2-(4-Methoxy-phenyl)-5-morpholin-4-yl-oxazolo[5,4-b]pyridine

Step 1: N-(2,6-Dichloro-pyridin-3-yl)-4-methoxy-benzamide

4-Methoxy-benzoyl chloride (4.15 mL, 30.7 mmol) was added dropwise to a stirred, cooled 0° C. mixture of 2,6-dichloro-pyridin-3-ylamine (5 g, 30.7 mmol) in pyridine (31 mL). Following addition, the reaction mixture was allowed to warm to room temperature and stirring was continued for 30 minutes, at which point the reaction mixture was poured into water causing the formation of a precipitate which was collected by filtration. The collected solids were washed with additional water before drying overnight in vacuo affording N-(2,6-dichloro-pyridin-3-yl)-4-methoxy-benzamide (8.66 g, 29.1 mmol, 95% yield) which was used in subsequent reactions without further purification. ES MS (M+H$^+$)=297.

Step 2: 5-Chloro-2-(4-methoxy-phenyl)-oxazolo[5,4-b]pyridine

N-(2,6-Dichloro-pyridin-3-yl)-4-methoxy-benzamide (3.86 g, 13.0 mmol) and K$_2$CO$_3$ (1.80 g, 13 mmol) were combined in DMF (15 mL) and heated by microwave to 160° C. for 30 minutes. The resulting mixture was poured into water (100 mL) causing the formation of a precipitate which was collected by filtration and washed with additional water before drying overnight in vacuo. The resulting solid was purified with silica gel flash chromatography (0-60% EtOAc in hexanes) to afford 5-chloro-2-(4-methoxy-phenyl)-oxazolo[5,4-b]pyridine (2.0 g, 7.67 mmol, 59.1% yield) which was used in subsequent reactions without further purification. ES MS (M+H$^+$)=261.

Step 3: 2-(4-Methoxy-phenyl)-5-morpholin-4-yl-oxazolo[5,4-b]pyridine

To a solution of 5-chloro-2-(4-methoxy-phenyl)-oxazolo[5,4-b]pyridine (25 mg, 0.096 mmol) in DMSO (1 mL) was added L-proline (11.04 mg, 0.096 mmol), CuI (18.27 mg, 0.096 mmol), morpholine (13 µL, 0.15 mmol) and K$_3$PO$_4$ (40.7 mg, 0.192 mmol). The reaction vessel was sealed and heated to 90° C. overnight, at which point the reaction was diluted with water and extracted with EtOAc. The organics were concentrated leaving a residue that was purified by reverse phase chromatography to afford 2-(4-methoxy-phenyl)-5-morpholin-4-yl-oxazolo[5,4-b]pyridine (4.3 mg, 0.013 mmol, 14% yield). ES MS (M+H$^+$)=312; $^1$H NMR (499 MHz, DMSO-d$_6$): δ 8.07-8.02 (d, J=8.7 Hz, 2H); 7.98-7.94 (m, 1 H); 7.17-7.11 (d, J=8.7 Hz, 2H); 6.91 (d, J=8.8 Hz, 1H); 3.86 (s, 3H); 3.73 (t, J=4.8 Hz, 4H); 3.51 (t, J=4.8 Hz, 4H); HRMS m/z 312.1352 (C$_{17}$H$_{17}$N$_3$O$_3$+H$^+$ requires 312.1343)

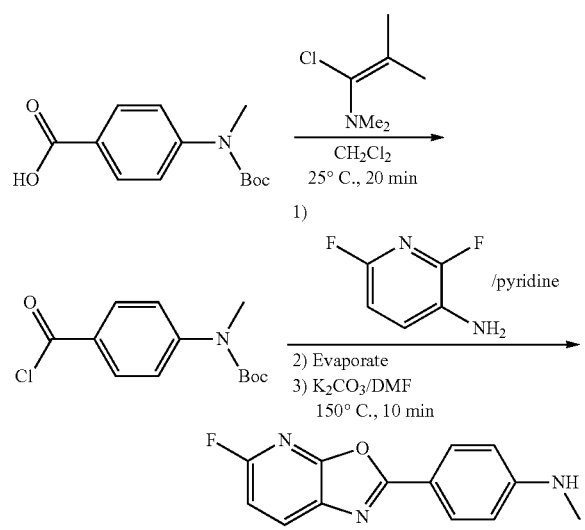

Scheme 3

EXAMPLE 3

[4-(5-Fluoro-oxazolo[5,4-b]pyridine-2-yl)-phenyl]methyl-amine

To a solution of 4-(text-butoxycarbonyl-methyl-amino)-benzoic acid (70 mg, 0.28 mmol) in CH$_2$Cl$_2$ (2 mL) was added 1-chloro-N,N-2-trimethylpropenylamine (98 µL, 0.74 mmol). Following formation of the resulting acid chloride, the reaction mixture was concentrated affording a residue that was dissolved in pyridine (2 mL) before 2,6-difluoro-pyridin-3-ylamine (30 mg, 0.23 mmol) was added in one portion. After an additional 30 minutes the reaction mixture was concentrated to dryness affording a residue to which was added DMF (2 mL) and K$_2$CO$_3$ (64 mg, 0.46 mmol). The resulting mixture was heated by microwave to 150° C. for 10 min, after which the resulting mixture was filtered, concentrated and purified by silica gel flash chromatography (0 to 100% EtOAc in hexanes) to afford [4-(5-fluoro-oxazolo[5,4-b]pyridine-2-yl)-phenyl]-methyl-amine (50 mg, 0.21 mmol, 89%). ES MS (M+H$^+$)=244; $^1$H NMR (300 MHz, DMSO-d$_6$): δ 8.24 (t, J=7.7 Hz, 1H); 7.89 (d, J=8.4 Hz, 2H); 7.18 (d, J=8.4 Hz, 1H); 6.68 (d, J=8.5 Hz, 3H); 2.76 (s, 3H); HRMS m/z 244.0883 (C$_{13}$H$_{10}$FN$_3$O+H$^+$ requires 244.0881).

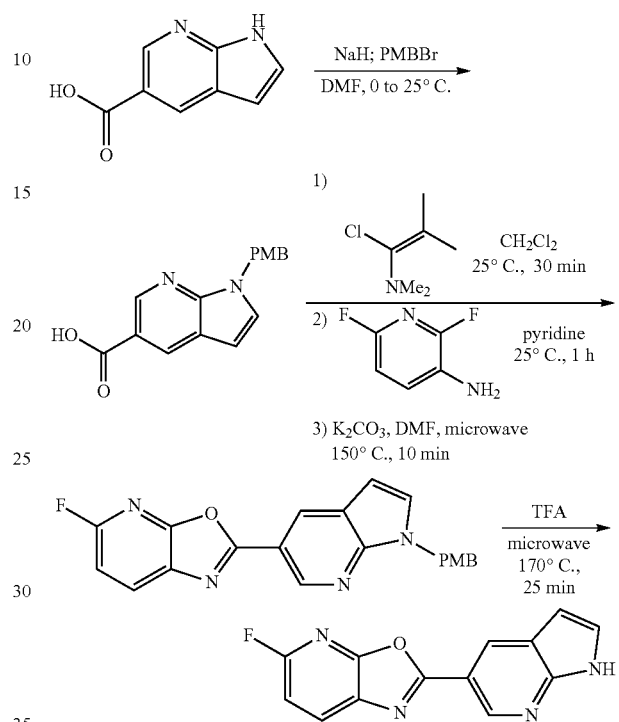

Scheme 4

EXAMPLE 4

5-Fluoro-2-(1H-pyrrolo[2,3-b]pyridin-5-yl)-oxazolo[5,4-b]pyridine

Step 1: 1-(4-Methoxy-benzyl)-1H-pyrrolo[2,3-b]pyridine-5-carboxylic acid

To a stirred cooled 0° C. suspension of NaH (272 mg, 6.81 mmol) in DMF (23 mL) was added 1H-pyrrolo[2,3-b]pyridine-5-carboxylic acid methyl ester (400 mg, 2.27 mmol). After 5 min, PMBBr (548 mg, 2.72 mmol) and KI (377 mg, 2.27 mmol) were added and the reaction mixture was allowed to warm to room temperature and stirring was continued overnight. The following day, water was added to quench the remaining NaiI and the aqueous mixture was washed with EtOAc, which was discarded. The aqueous phase was collected and carefully acidified (pH ~3) before extraction with EtOAc. The combined organics were dried and evaporated to afford 1-(4-methoxy-benzyl)-1H-pyrrolo[2,3-b]pyridine-5-carboxylic acid (160 mg, 0.57 mmol, 25% yield). ES MS (M+H$^+$)=283.

Step 2: 5-Fluoro-2-[1-(4-methoxy-benzyl)-1H-pyrrolo[2,3-b]pyridin-5-yl]-oxazolo[5,4-b]pyridine To a stirred solution of 1-(4-methoxy-benzyl)-1H-pyrrolo[2,3-b]pyridine-5-carboxylic acid (47 mg, 0.17 mmol) in CH$_2$Cl$_2$ (2 mL) was added 1-chloro-N,N-2-trimethylpropenylamine (45 µL, 0.34 mmol). Following formation of the resulting acid chloride, the reaction mixture was concentrated affording a residue that was dissolved in pyridine (2 mL) before 2,6-difluoro-pyridin-3-ylamine (20 mg, 0.15 mmol)

was added in one portion. After an additional 30 minutes the reaction mixture was concentrated to dryness affording a residue, to which was added DMF (2 mL) and K$_2$CO$_3$ (64 mg, 0.46 mmol). The resulting mixture was heated by microwave to 150° C. for 10 min, after which the resulting mixture was filtered and concentrated, affording 5-fluoro-2-[1-(4-methoxy-benzyl)-1H-pyrrolo[2,3-b]pyridin-5-yl]-oxazolo[5,4-b]pyridine as a crude residue which was subsequently used without further purification. ES MS (M+H$^+$)=375.

Step 3: 5-Fluoro-2-(1H-pyrrolo[2,3-b]pyridin-5-yl)-oxazolo[5,4-b]pyridine

Crude 5-fluoro-2-[1-(4-methoxy-benzyl)-1H-pyrrolo[2,3-b]pyridin-5-yl]-oxazolo[5,4-b]pyridine from Step 2 was dissolved in TFA (0.5 mL) and heated by microwave to 170° C. for 25 min. The volatiles were then removed in vacuo and the resulting residue was purified by HPLC to afford 5-fluoro-2-(1H-pyrrolo[2,3-b]pyridin-5-yl)-oxazolo[5,4-b]pyridine (2.5 mg, 9.8 µmol, 6% yield). ES MS (M+H$^+$)=255; $^1$H NMR δ (ppm) (DMSO-d$_6$): 12.18 (1H, s), 9.04 (1H, d, J=2.10 Hz), 8.76 (1H, d, J=2.06 Hz), 8.44 (1H, dd, J=8.39, 7.10 Hz), 7.67 (1H, t, J=2.75 Hz), 7.31 (1H, d, J=8.40 Hz), 6.68 (1H, d, J=3.43 Hz); HRMS m/z 255.0675 (C$_{13}$H$_7$FN$_4$O+H$^+$ requires 255.0677).

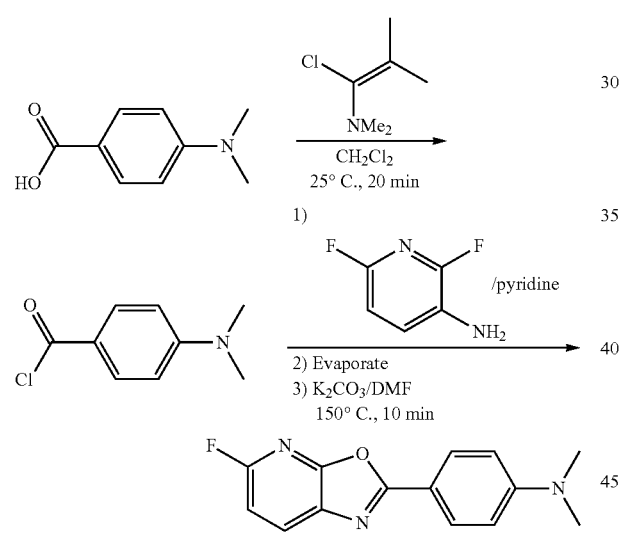

Scheme 5

EXAMPLE 5

[4-5-Fluoro-oxazolo[5,4-b]-pyridin-2-yl)-phenyl]-dimethyl-amine

To a solution of 4-dimethylamino-benzoic acid (635 mg, 3.84 mmol) in CH$_2$Cl$_2$ (38 mL) was added 1-chloro-N,N-2-trimethylpropenylamine (0.51 mL, 3.84 mmol). Following formation of the resulting acid chloride, the reaction mixture was concentrated affording a residue that was dissolved in pyridine (7.8 mL) before 2,6-difluoro-pyridin-3-ylamine (500 mg, 3.84) was added in one portion. After an additional 1 h, the reaction mixture was concentrated to dryness affording a residue to which was added DMF (5 mL) and K$_2$CO$_3$ (531 mg, 3.84 mmol). The resulting mixture was heated by microwave to 150° C. for 10 min, after which the resulting mixture was filtered, concentrated and purified by silica gel flash chromatography (0 to 100% EtOAc in hexanes) to afford [4-(5-fluoro-oxazolo[5,4-b]pyridin-2-yl)-phenyl]-dimethyl-amine (430 mg, 1.67 mmol, 44%). ES MS (M+H$^+$)=258; $^1$H NMR δ (ppm)(DMSO-d$_6$): 8.28 (1H, dd, J=8.36, 7.14 Hz), 8.01-7.94 (2H, m), 7.24-7.18 (1H, m), 6.87 (2H, d, J=8.89 Hz), 3.05 (6H, s); HRMS m/z 258.1039 (C$_{14}$H$_{12}$FN$_3$O+H$^+$ requires 258.1037).

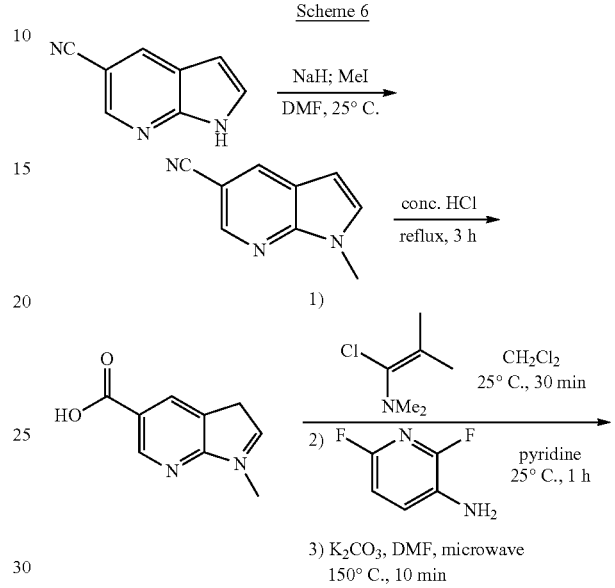

Scheme 6

EXAMPLE 6

5-Fluoro-2-(1-methyl-1H-pyrrolo[2,3-b]pyridin-5-yl)-oxazolo[5,4-b]pyridine

Step 1: 1-Methyl-1H-pyrrolo[2,3-b]pyridine-5-carbonitrile

To a stirred solution of 1H-Pyrrolo[2,3-b]pyridine-5-carbonitrile (2.88 g, 20.1 mmol) in DMF (40 mL) was added 60% NaH (2.41 g, 60.4 mmol). After 20 minutes, iodomethane was added in one portion (6.3 mL, 101 mmol) and the resulting mixture was stirred overnight. The following day, water was carefully added drop-wise to quench the remaining NaH before additional water was added (50 mL) causing precipitation of the product. Filtration and drying in vacuo afforded 1-methyl-1H-pyrrolo[2,3-b]pyridine-5-carbonitrile (3.16 g, 20.1 mmol, 100% yield) which was subsequently used without further purification. ES MS (M+H$^+$)=158.

Step 2: 1-Methyl-1H-pyrrolo[2,3-b]pyridine-5-carboxylic acid

1-Methyl-1H-pyrrolo[2,3-b]pyridine-5-carbonitrile (3.16 g, 20.1 mmol) was dissolved in concentrated aqueous HCl (15 mL) and refluxed for 3 h. After cooling, the mixture was evaporated in vacuo affording 1-methyl-1H-pyrrolo[2,3-b]pyridine-5-carboxylic acid (3.54 g, 20.1 mmol, 100% yield) which was subsequently used without further purification. ES MS (M+H$^+$)=177.

Step 3: 5-Fluoro-2-(1-methyl-1H-pyrrolo[2,3-b]pyridin-5-yl)-oxazolo[5,4-b]pyridine To a suspension of 1-methyl-1H-pyrrolo[2,3-b]pyridine-5-carboxylic acid (68 mg, 0.38 mmol) in $CH_2Cl_2$ (2 mL) was added 1-chloro-N,N-2-trimethylpropenylamine (50 μL, 0.38 mmol). Following formation of the resulting acid chloride, the reaction mixture was concentrated affording a residue that was dissolved in pyridine (2 mL) before 2,6-difluoro-pyridin-3-ylamine (50 mg, 0.38 mmol) was added in one portion. After an additional 30 minutes the reaction mixture was concentrated to dryness affording a residue, to which was added DMF (2 mL) and $K_2CO_3$ (53 mg, 0.38 mmol). The resulting mixture was heated by microwave to 150° C. for 10 min, after which the resulting mixture was filtered and concentrated. The resulting residue was purified by reverse phase chromatography affording 5-fluoro-2-(1-methyl-1H-pyrrolo[2,3-b]pyridin-5-yl)-oxazolo[5,4-b]pyridine (13.1 mg, 0.049 mmol, 13% yield). ES MS (M+H$^+$)=269; $^1$H NMR δ (ppm)(DMSO-d$_6$): 9.07 (1H, d, J=2.12 Hz), 8.75 (1H, d, J=2.13 Hz), 8.42 (1H, t, J=7.74 Hz), 7.70 (1H, d, J=3.52 Hz), 7.29 (1H, d, J=8.41 Hz), 6.69 (1H, d, J=3.52 Hz), 3.89 (3H, s); HRMS m/z 269.0831 ($C_{14}H_9FN_4O$+H$^+$ requires 269.0833).

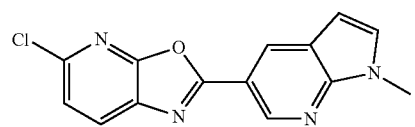

EXAMPLE 7

5-Chloro-2-(1-methyl-1H-pyrrolo[2,3-b]pyridine-5-yl)-axazolo[5,4-b]pyridine

To a suspension of 1-methyl-1H-pyrrolo[2,3-b]pyridine-5-carboxylic acid (200 mg, 1.14 mmol) in $CH_2Cl_2$ (4 mL) was added 1-chloro-N,N-2-trimethylpropenylamine (600 μL, 4.54 mmol). Following formation of the resulting acid chloride, the reaction mixture was concentrated affording a residue that was dissolved in pyridine (4 mL) before 2,6-dichloro-pyridin-3-ylamine (278 mg, 1.70 mmol) was added in one portion. After an additional 30 minutes the reaction mixture was concentrated to dryness affording a residue, to which was added DMA (3 mL) and $Cs_2CO_3$ (552 mg, 1.70 mmol). The resulting mixture was heated by microwave to 165° C. for 15 min, after which the resulting mixture was filtered and concentrated. The resulting residue was purified by reverse phase chromatography affording 5-fluoro-2-(1-methyl-1H-pyrrolo[2,3b]-pyridine-5-yl)-oxazolo[5,4-b]pyridine (65 mg, 0.228 mmol, 20% yield). ES MS (M+H$^+$)=285; $^1$H NMR δ (ppm) (DMSO-d$_6$): 9.10 (1H, s), 8.78 (1H, d, J2.29 Hz), 8.32 (1H, d, J=8.17 Hz), 7.75-7.59 (2H, m), 6.72 (1H, d, J=3.55 Hz), 3.91 (3H, s).

Scheme 7

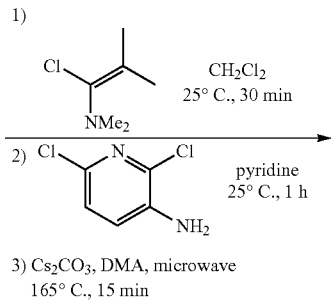

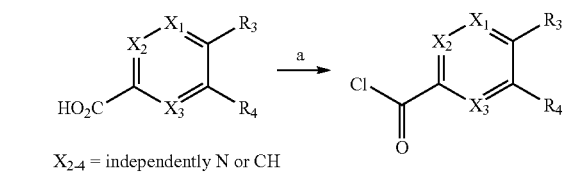

General Reaction Scheme 3

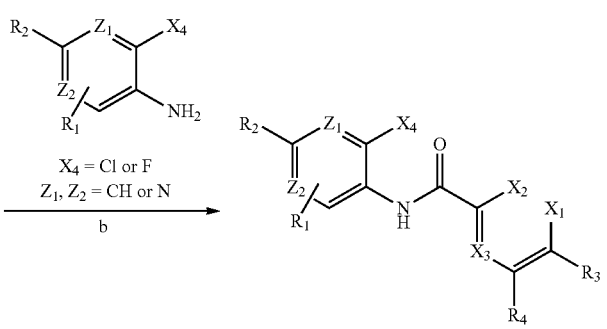

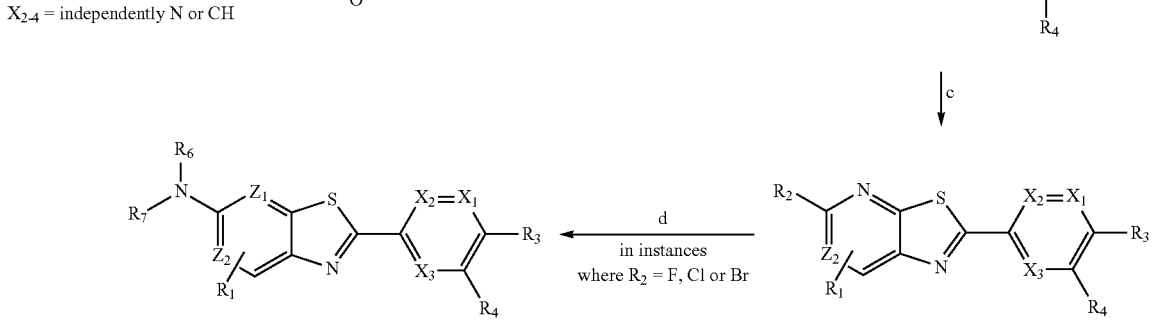

a) 1-Chloro-N,N-2-trimethyl-1-propenylamine or (COCl)$_2$, cat. DMF; b) pyridine; c) Lawesson's reagent, heat; d) R$_6$R$_7$NH, Cs$_2$CO$_3$ or Pd cat., R$_6$R$_7$NH As illustrated in General Reaction Scheme 3, suitably substituted carboxylic acids can be reacted with 1-chloro-N,N-2-trimethyl-1-propenylamine or oxalyl chloride and catalytic DMF to generate acid chlorides which in turn are reacted with suitably substituted 2-halo-3-amino pyridines to provide the corresponding amides, which are then converted into the corresponding 7-azabenzthiazoles or 4-azabenzthiazoles upon reaction with Lawesson's reagent at elevated temperature. In some instances, the carboxylic acid starting material may contain a Boc or PMB protecting group, which may be subsequently removed upon reaction with trifluoroacetic acid and/or heating to afford the final material. In this instance, all carboxylic acids, 2-amino-phenols, and 3-amino-2-pyridones were commercially available or were prepared using procedures known to those skilled in the art.

Scheme 8

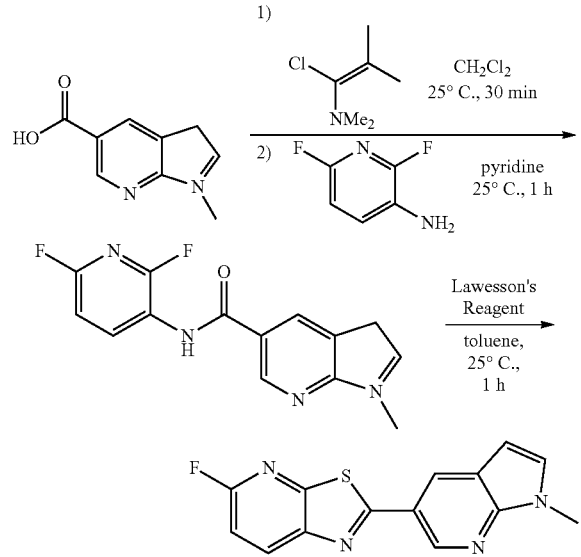

EXAMPLE 8

5-Fluoro-2-(1-methyl-1H-pyrrolo[2,3-b]pyridin-5-thiazolo[5,4-b]pyridine

Step 1: 1-Methyl-1H-pyrrolo[2,3-b]pyridine-5-carboxylic acid (2,6-difluoro-pyridin-3-yl)-amide To a suspension of 1-methyl-1H-pyrrolo[2,3-b]pyridine-5-carboxylic acid (3.54 g, 20.1 mmol) in $CH_2Cl_2$ (400 mL) was added 1-chloro-N,N-2-trimethylpropenylamine (5.26 mL, 40.2 mmol). Following formation of the resulting acid chloride, the reaction mixture was concentrated affording a residue that was dissolved in pyridine (100 mL) before 2,6-difluoro-pyridin-3-ylamine (2.61 mg, 20.1 mmol) was added in one portion. After an additional 30 minutes the reaction mixture was concentrated to dryness affording a residue, to which was added water causing precipitation of analytically pure 1-methyl-1H-pyrrolo[2,3-b]pyridine-5-carboxylic acid (2,6-difluoro-pyridin-3-yl)-amide (4.2 g, 72.5% yield). ES MS (M+H$^+$)=289.

Step 2: 5-Fluoro-2-(1-methyl-1H-pyrrolo[2,3-b]pyridin-5-yl)-thiazolo[5,4-b]pyridine To a suspension of 1-methyl-1H-pyrrolo[2,3-b]pyridine-5-carboxylic acid (2,6-difluoro-pyridin-3-yl)-amide (300 mg, 1.04 mmol) in toluene in a sealable vial was added Lawesson's Reagent (210 mg, 0.52 mmol). The vial was capped and heated to 130° C. for 12 h, cooled to room temp, and loaded directly onto a silica gel column and purified by flash column chromatography (0 to 100% EtOAc in hexanes) to afford 5-fluoro-2-(1-methyl-1H-pyrrolo[2,3-b]pyridin-5-yl)-thiazolo[5,4-b]pyridine (247 mg, 83% yield). ES MS (M+H$^+$)=285; $^1$H NMR δ (ppm)(DMSO-d$_6$): 8.99 (1H, d, J=2.23 Hz), 8.64 (1H, s), 8.66-8.53 (1H, m), 7.67 (1H, d, J=3.50 Hz), 7.38 (1H, dd, J=8.74, 1.80 Hz), 6.65 (1H, d, J=3.49 Hz), 3.87 (3H, s).

Scheme 9

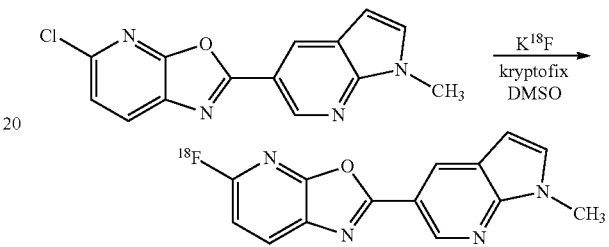

EXAMPLE 9

Radiochemical Synthesis of [$^{18}$F]5-fluoro-2-(1-methyl-1H-pyrrolo [2,3-b]pyridin-5-yl)-oxazolo[5,4-b]pyridine

[$^{18}$F]F$^-$ was obtained from Siemens Biomarker Solutions (North Wales, Pa.). The [$^{18}$F]F$^-$ was produced via the $^{18}$O(p, n)$^{18}$F reaction by using $^{18}$O-enriched water (Cambridge Isotope Laboratories). At the end of the bombardment, the contents of the tantalum target was emptied, trapped on a small anion exchange resin, and transported to the radiochemistry lab and eluted before use. Radiochemical procedures were carried out by using a Gilson 233XL liquid handler. The [$^{18}$F]F$^-$ containing anion exchange resin was eluted with a mixture (0.7 mL) of 80% acetonitrile:20% oxalate solution [0.05 mL of (200 mg of $K_2C_2O_4$/3 mg of $K_2CO_3$/5 mL of $H_2O$)+0.25 mL of $H_2O$+1.2 mL of MeCN] and added to a 1 mL v-vial in the microwave cavity. This vial was vented using an 18G1 syringe needle. To the aqueous fluoride solution was added Kryptofix222 (0.15 mL, 36 mg/mL MeCN) and the fluoride was dried under argon flow using microwave pulses (~50 W) to heat the aqueous acetonitrile. Additional aliquots of acetonitrile (2×0.5 mL) were added for azeotropic drying. A solution of 5-chloro-2-(1-methyl-1H-pyrrolo[2,3-b]pyridin-5-yl)-oxazolo[5,4-b]pyridine (2 mg) in DMSO (0.25 mL) was added to the microwave vial, and the reaction mixture was pulsed with the microwave for 200 sec (~60 W, 140° C.). After cooling for 1 min, the reaction was diluted with acetonitrile/water (0.4 mL, 60:40) and purified by semi prep HPLC system (Gemni RP C18 column, 7.8×150 mm, 5 μm). The solvent system used was 45:55 acetonitrile:$Na_2HPO_4$ (0.1 N) at 5 mL/min and the retention time was ~9 min. The peak corresponding to 5-fluoro-2-(1-methyl-1H-pyrrolo[2,3-b]pyridin-5-yl)-oxazolo[5,4-b]pyridine was collected, most of the solvent was removed in vacuo, and transferred to a capped vial using physiologic saline as a rinse to give 51 mCi of [$^{18}$F] 5-fluoro-2-(1-methyl-1H-pyrrolo[2,3-b]pyridin-5-yl)-oxazolo[5,4-b]pyridine with a specific activity of 3,229 Ci/mmol and a radiochemical purity of >99% (n=11). The specific activity for [$^{18}$F] 5-fluoro-2-(1-methyl-1H-pyrrolo[2,3-b]pyridin-5-yl)-oxazolo[5,4-b]pyridine was determined by counting an aliquot in a dose calibrator and determining the mass by analytical HPLC system (C18 XTerra RP18, 4.6×150 mm, 5 μm) against an authentic standard. The solvent system used was 50:50 acetonitrile:Na$_2$HPO$_4$ (0.1 N) at 1 mL/min and the retention time was ~5 min.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

Biological Examples

Homogenates from AD and non-AD human brain samples were assessed for their immunoreactivity to anti-Aβ antibody 6E10. The highest and lowest levels of 6E10 immunoreactivity were chosen for the AD group and the non-AD control group, respectively. Candidate Aβ compounds were initially selected based on their structural similarity to published amyloid ligands and then for high affinity in competing with [$^3$H]PIB binding to AD brain homogenates. These compounds were radiolabeled with [$^3$H] and tested for binding affinity to human AD brain homogenates as well as binding to human non-AD brain homogenates. [$^3$H]-DMAB (see structure below) was selected based from these candidates based on its binding affinity for human AD brain homogenates, and minimal binding to non-AD control homogenates. A low fraction of non-displaceable binding was also an important criterion.

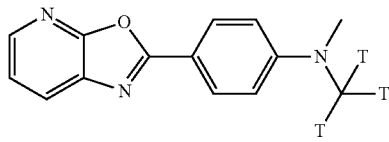

Structure of [$^3$H]—DMAB
(T = tritium)

PET radiotracer candidate compounds were then selected based on their high affinity competition with [$^3$H]-DMAB in binding to AD brain homogenates. These PET radiotracer candidate compounds were tested to determine if they were effective PgP substrates. Those PET radiotracer candidate compounds with little PgP substrate activity were radiolabeled with [$^3$H] or [$^{18}$F] and tested for binding affinity to human AD brain homogenates as well as binding to human non-AD brain homogenates and in autoradiographic studies using human AD and non-AD brain slices. Candidate radioligands were selected based on their strong binding affinity for human AD brain homogenates, and minimal binding to non-AD control homogenates. A low fraction of non-displaceable binding was also an important criterion. Minimization of white matter binding was an important criterion. Counterscreening indicated these compounds were also potent inhibitors of MAO-B, a mitochondrial enzyme expressed in platelets and astrocytes.

Tissue Homogenate Binding Assay:

Postmortem frozen human brain samples from donors with clinical diagnosis of Alzheimer's diseases (AD) or normal control subjects (non-AD) were purchased from Analytical Biological Services Inc., at 701-4 Cornell Business Park, Wilmington, Del. 19801. Brain homogenates of frontal cortex were prepared, divided into aliquots and stored at −70° C. prior to use.

[$^3$H]-DMAB was synthesized at a specific activity of ~80 Ci/nmol. The final concentration of radioligand for tissue homogenate binding assay was 1.5 nM. Brain homogenates were diluted with phosphate buffered saline (PBS) to 0.4 mg/mL from original 10 mg/mL volume and 200 μl was used in assay for a final concentration of 50 μg/assay tube. Unlabeled test compounds were dissolved in dimethylsulfoxide (DMSO) at 1 mM. Dilution of test compound to various concentrations was made with PBS containing 2% DMSO. Total binding was defined in the absence of competing compound, and non-displaceable binding was determined in the presence of 1 μM unlabeled self block. Compound dilutions (10×) were added into the assay tube (25 μL each/per tube, separately) containing 200 μL brain homogenate dilution, and the tubes were pre-incubated at room temperature for 10 minutes. Then radioligand dilutions (10×) were added into the assay tube (25 μL each/per tube, separately) to a final volume of 250 μL per tube. Incubation was carried out at room temperature (25° C.) for 90 minutes, and then the assay samples were filtered onto GF/C filters using Skatron 12 well harvester, washing on setting 5-5-5 (~3×2 ml) ice cold buffer (PBS, pH 7.4). GF/C filter papers for the Skatron harvester were pre-soaked in 0.1% BSA for 1 hour at room temperature before use. Filters were punched into scintillation vials and counted in 2 mL Ultima Gold on Perkin Elmer Tri-Carb 2900TR for 1 minute. The data analysis was done with Prism software. All assays were done in triplicate, and in the laboratory designated for studies using human tissues.

Monoamine Oxidase B Assays:

Functional assay: MAO-B containing membrane fractions prepared from insect cells expressing human MAO-B (BD Supersomes Enzymes, BD Biosciences Discovery Labware, Woburn Mass.) were used as a source of MAO-B. Assays were conducted in 96-well plates in a final volume of 200 μL. The assay buffer was 0.1 M potassium phosphate (pH 7.4). The assay system consisted of three mixes: a) inhibitor dilution mix, which was the assay buffer, b) substrate/buffer/control insect cell protein mix: 4× substrate-80 μM kynuramine and 4× control insect cell protein, and c) enzyme/buffer mix: 4× concentrate of MAO-B prepared in assay buffer. The final MAO-B concentration was 0.015 mg/mL. The final total, normalized protein concentration, using control insect protein, was 0.06 mg/mL. Test compounds were serial diluted 3-fold in the inhibitor dilution mix directly in the 96-well plate (total final volume of 100 μL). Fifty μL of the substrate/buffer mix was added to each well. The 96-well plate, containing test compound and MAO substrate (150 μL it total volume), was preincubated to 37° C. The reaction was initiated with 50 μL of enzyme/buffer mix. Reactions were stopped after 20 min by addition of 75 μL of 2 N NaOH. The excitation/emission wavelengths were 330/460 nm (20 nm slit width). (NOTE: the optimal wavelengths for detecting 4-hydroxyquinoline are approximately 310 nm excitation and 380 nm emission). Product formation was quantified by comparing the fluorescence emission of the samples to that of known amounts of authentic metabolite standard, 4-hydroxyquinoline, the product formed from kynuramine deamination. All test compounds were dissolved in DMSO.

Radioligand binding assay: MAO-B containing membrane fractions prepared from insect cells expressing human MAO-B (BD Supersomes Enzymes, BD Biosciences Discovery Labware, Woburn Mass.) were used as a source of MAO-B. [$^3$H]-DMAB or [$^3$H] 5-Fluoro-2-(1-methyl-1H-indazol-5-yl)-oxazolo[5,4-b]pyridine were synthesized at a specific activity of ~80 Ci/mmol. The final concentration of radioligand for tissue homogenate binding assay was 8-10 nM. MAO-B membrane fractions were diluted with phosphate buffered saline (PBS) to 0.25 mg/mL from original 5 mg/mL volume and 200 µl was used in assay for a final mass of 50 µg/assay tube. Unlabeled test compounds were dissolved in dimethylsulfoxide (DMSO) at 1 mM. Dilution of test compound to various concentrations was made with PBS containing 2% DMSO. Total binding was defined in the absence of competing compound, and non-displaceable binding was determined in the presence of 1 µM unlabeled self block. Compound dilutions (10×) were added into the assay tube (25 µL each/per tube, separately) containing 200 µL diluted MAO-B membrane fraction, and the tubes were pre-incubated at room temperature for 10 minutes. Then radioligand dilutions (10×) were added into the assay tube (25 µL each/per tube, separately) to a final volume of 250 µL per tube. Incubation was carried out at room temperature (25° C.) for 90 minutes, and then the assay samples were filtered onto GF/C filters using Skatron 12 well harvester, washing on setting 5-5-5 (~3×2 ml) ice cold buffer (PBS, pH 7.4). GF/C filter papers for the Skatron harvester were pre-soaked in 0.1% BSA for 1 hour at room temperature before use. Filters were punched into scintillation vials and counted in 2 mL Ultima Gold on Perkin Elmer Tri-Carb 2900TR for 1 minute. The data analysis was done with Prism software. All assays were done in triplicate, and in the laboratory designated for studies using human tissues.

In vitro Autoradiography:

Postmortem frozen human brain samples from donors with clinical diagnosis of Alzheimer's diseases (AD) or normal control subjects (non-AD) were purchased from a commercial source. Frozen brain slices (20 µm thickness) were prepared using a cryostat (Leica CM3050) and kept in sequential order. The tissue slices were placed on Superfrost Plus glass slides (Cat. #5075-FR, Brain Research Laboratories, USA), dried at room temperature, and stored in a slide box at −70° C. before use. The final concentration of radioligand for in vitro autoradiography was 1.0 nM. On the day of a binding experiment, adjacent slices were selected from each brain region of interest for in vitro autoradiographic study, and were designated as total binding and non-specific binding (NSB). These slices were thawed at room temperature for 15 minutes in a biosafety hood. Total binding of radioligand in brain slices was defined in the absence of competitor, and non-specific binding (NSB) was determined in the presence of competitor (1.0 µM unlabeled compound). The brain slides were first pre-incubated at room temperature for twenty minutes in PBS buffer, pH 7.4. The slices were then transferred to fresh buffer containing radioligand or radioligand plus competitor as described above, and incubated at room temperature for ninety minutes. Incubation was terminated by washing the slices three times in ice cold (4° C.) wash buffer (PBS, pH 7.4) with each wash lasting three minutes. After washing, the slices were briefly rinsed in ice cold (4° C.) deionized water, and then dried completely by an air blower at room temperature. The slices were placed against Fuji Phosphor Image Plates (TR25, Fuji) in a sealed cassette for exposure at room temperature. After one week exposure, the plates were scanned in Fuji BAS 5000 Scanner, and the scanned images were analyzed using MCID 7.0 software. [$^3$H]-microscales (Amersham Biosciences, GE), were used for quantification of radioligand binding density. All the slice binding assays were done in the laboratory designated for studies using human tissues.

Candidate radioligands that fit these criteria were radiolabeled with [$^{18}$F]. The [$^{18}$F] labeled radioligands were characterized in vivo in rhesus monkey for rapid uptake into and clearance from brain. In selecting the final PET radiotracer, minimization of binding potential in white matter was an important criterion as well as high brain uptake, defined as >1.5 SUV.

PET Imaging in Rhesus Monkeys

All studies were conducted under the guiding principles of the American Physiological Society and the Guide for the Care and Use for Laboratory Animals published by the US National Institutes of Health (NIH publication No 85-23, revised 1985) and were approved by the West Point Institutional Animals Care and Use Committee at Merck Research Laboratories. Rhesus monkeys (~10 kg) were initially anesthetized with ketamine (10 mg/kg i.m.), then induced with propofol (5 mg/kg i.v.), intubated, and respired with medical grade air. Body temperature was maintained with circulating water heating pads, and temperature, $SpO_2$, and end-tidal $CO_2$ were monitored for the duration of the study. Anesthesia was maintained with propofol (0.4 mg/kg/min) for the duration of the study. PET scans were performed on an ECAT EXACT HR+ (CTI/Siemens, Knoxville, Tenn.) in 3D mode; transmission data (for subsequent attenuation correction) were acquired in 2D mode before injection of the radiopharmaceutical. Emission scans were performed immediately following bolus injection of ~5 mCi of each PET tracer. The emission scans were corrected for attenuation, scatter, and dead time and reconstructed with a ramp filter, resulting in transverse and axial spatial resolution of _5 mm at FWHM.

For each scan a static (or summed) PET image was obtained by summing the dynamic frames acquired during the acquisition. Regions of interest (ROIs) were drawn on the summed PET images using an MRI image for anatomical identification. Then ROIs were projected onto the dynamic scans to obtain the corresponding time-activity curves (TACs). TACs were expressed in standard uptake value (SUV) units using the monkey body weight and the tracer injected dose as: TAC (SUV)=1,000×TAC (Bq)×weight (kg)/injected tracer dose (Bq).

Assessment of Amyloid Load:

Subjects are administered a Mini-Mental State Examination to assess whether they are normal control subjects or are AD patients. PET studies are performed on both groups of patients using the PET radiotracers described herein, and using methods known to those versed in the art. Uptake and retention of radiotracer in regions where amyloid plaque is known to accumulate (e.g., frontal cortical regions) is compared with uptake and retention of radiotracer in a reference region where amyloid plaque does not accumulate (e.g., cerebellum). The difference in uptake and retention between these pairs of regions is greater for the AD patients compared to the normal control subjects; this greater difference is due to the greater AP plaque load in the AD patients. Test-retest (intra-subject) variability is established by a second, essentially identical PET study.

To determine if a compound is effective for reducing amyloid plaque, a PET study is performed prior to administering the plaque reducing compound. After a course of treatment with the therapeutic compound, a second PET study is performed. A reduction in uptake and retention of the PET radiotracer in the regions in which plaque is known to accumulate (greater than the test-retest variability) indicates a reduction in the plaque load. In such a study each subject serves as his or her own pretreatment control.

The compounds of this invention possess IC50 values in the human AD brain tissue homogenate assay in the range of 0.1 nM-1000 nM. For example, the IC50 of the following compounds are:

| Compound | IC50 in Tissue Homogenate Assay |
| --- | --- |
| 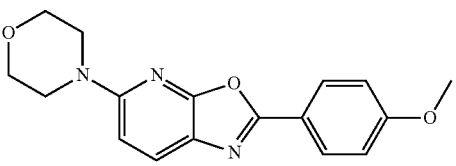 [SMILES: COc1ccc(-c2nc3ccc(N4CCOCC4)nc3o2)cc1] | 350 nM |
| 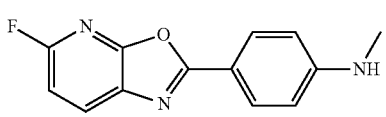 [SMILES: CNc1ccc(-c2nc3ccc(F)nc3o2)cc1] | 17 nM |
| 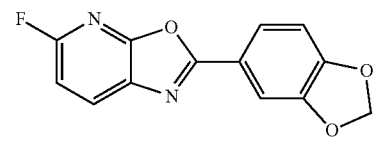 | 36 nM |
| 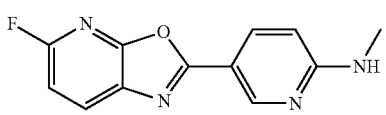 [SMILES: CNc1ccc(-c2nc3ccc(F)nc3o2)cn1] | 104 nM |
| 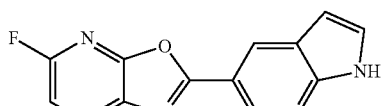 | 22 nM |

The compounds of this invention inhibit MAO-B activity or bind to MAO-B in the range of 0.1 nM-1000 nM. For example, the following compounds demonstrate MAO-B inhibition or binding:

| Compound | MAO-B Activity |
| --- | --- |
| 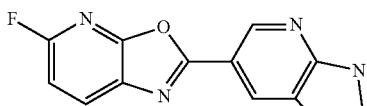 | Ki = 18 nM in functional assay |
| 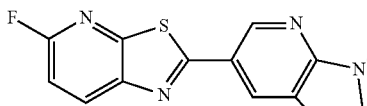 | IC50 = 3.7 nM in binding assay |
| 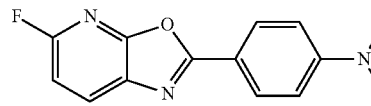 | IC50 = 31 nM in binding assay |

What is claimed is:

1. A compound represented by Formula I:

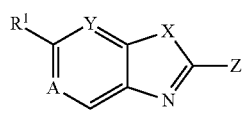

or a pharmaceutically acceptable salt, solvate or in vivo hydrolysable ester thereof, wherein:

Y is N;
A is N, or CH;
X is O or S;
Z is selected from the group consisting of benzothiazolyl, indolyl, pyrazolopyridinyl, and pyrrolopyridinyl all optionally substituted with 1 to 3 groups of $R^2$, $R^3$ or $R^4$, provided that when $R^1$ is hydrogen or —(CH$_2$)$_n$halo and Z is benzothiazolyl, then the $R^2$, $R^3$ and $R^4$ substituents on the benzothiazolyl cannot be hydrogen, —(CH$_2$)$_n$halo, —C$_{1-6}$alkyl, —CF$_3$, or —(CH$_2$)$_n$OR;
R represents hydrogen, or —C$_{1-6}$alkyl;
$R^1$ represents hydrogen, —C$_{5-10}$ heterocyclyl, —N(R$^2$)$_2$, CN, —(CH$_2$)$_n$halo, CF$_3$, —O(CH$_2$)$_n$R, O(CH$_2$)$_n$C$_{5-10}$ heterocyclyl, —C$_{1-6}$alkyl, —OCF$_3$, —O(CH$_2$)$_n$F, —(O(CH$_2$)$_s$)$_p$halo, —(O(CH$_2$)$_s$)$_p$OR, —C(O)OR, or heterospirocycle said alkyl, and heterocyclyl optionally substituted with 1 to 3 groups of $R^a$, with the proviso that $R^1$, $R^2$, $R^3$ and $R^4$ are not hydrogen at the same time;
$R^2$, $R^3$ and $R^4$ independently represent hydrogen, —(CH$_2$)$_n$halo, —C$_{1-6}$alkyl, —CF$_3$, —(CH$_2$)$_n$OR, (CH$_2$)$_n$C$_{5\text{-}10}$ heterocyclyl, —N(R)$_2$, said alkyl, and heterocyclyl optionally substituted with 1 to 3 groups of R$^a$;

R$^a$ represents —CN, NO$_2$, halo, CF$_3$, —C$_{1\text{-}6}$alkyl, —C$_{1\text{-}6}$alkenyl, —C$_{1\text{-}6}$alkynyl, —(CH$_2$)$_n$halo, —OR, —NRR$^1$, —C(=NR$^1$)NR$^2$R$^3$, —N(=NR$^1$)NR$^2$R$^3$, —NR$^i$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$;

n represents 0-6;
s represents 2-4; and
p represents 1-3.

2. The compound according to claim 1 wherein Z is selected from the group consisting of:

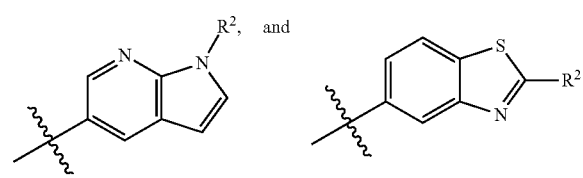

or a pharmaceutically acceptable salt, solvate or in vivo hydrolysable ester thereof.

3. The compound according to claim 1 wherein R$^1$ is selected from the group consisting of —C$_{5\text{-}10}$ heterocyclyl, —N(R$^2$)$_2$, —(CH$_2$)$_n$halo, —O(CH$_2$)$_n$C$_{5\text{-}10}$ heterocyclyl, —(O(CH$_2$)$_s$)$_p$halo, and —(O(CH$_2$)$_s$)$_p$OR.

4. The compound according to claim 1 wherein the compounds of formula I are $^2$11, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$CL, $^{82}$Br, $^{76}$Br, $^{77}$Br, $^{123}$I, $^{124}$I and $^{131}$I isotopically labeled.

5. The compound according to claim 1 of structural formula Ia:

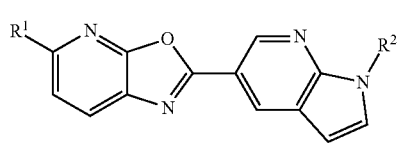

or a pharmaceutically acceptable salt, solvate or in vivo hydrolysable ester thereof.

6. The compound according to claim 1 of structural formula Ic:

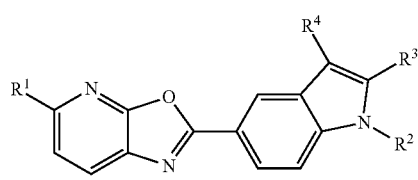

or a pharmaceutically acceptable salt, solvate or in vivo hydrolysable ester thereof.

7. A compound which is:
N-(2-methoxyethyl)-2-[4-(methylamino)phenyl][1,3]oxazolo[5,4-b]pyridin-5-amine,
N-methyl-4-[5-(2-methylmorpholin-4-yl)[1,3]oxazolo[5,4-b]pyridin-2-yl]aniline,
N-methyl-4-(5-pyrrolidin-1-yl[1,3]oxazolo[5,4-b]pyridin-2-yl)aniline,
5-fluoro-2-(2-methyl-1,3-benzothiazol-6-yl)[1,3]oxazolo[5,4-b]pyridine,
5-fluoro-2-(1-methyl-1H-indo1-5-yl)[1,3]oxazolo [5,4-b]pyridine,
2-(1,3-benzothiazol-6-yl)-5-fluoro[1,3]oxazolo[5,4-b]pyridine,
2-(2,3-dimethyl-1H-indol-5-yl)-5-fluoro[1,3]oxazolo[5,4-b]pyridine,
5-fluoro-2-[1-(1-methylethyl)-1H-pyrazolo[3,4-b]pyridin-5-yl][1,3]oxazolo[5,4-b]pyridine,
5-fluoro-2-(1H-indol5-yl)[1,3]oxazolo[5,4-b]pyridine,
5-fluoro-2-(1H-pyrrolo[2,3-b]pyridin-5-yl)[1,3]oxazolo [5,4-b]pyridine,
[5-(5-Fluoro-oxazolo[5,4-b]pyridin-2-yl)-pyridin-2-yl]-methyl-amine,
[5-(5-Fluoro-oxazolo[5,4-b]pyridin-2-yl)-pyridin-2-yl]-dimethyl-amine,
5-Fluoro-2-(6-[1,2,4]triazol-1-yl-pyridin-3-yl)-oxazolo [5,4-b]pyridine,
5-Fluoro-2-(1-methyl-1H-pyrrolo [2,3 -b]pyridin-5 -yl)-oxazolo [5,4-b]pyridine,
5-chloro-2-(1-methyl-1H-pyrrolo [2,3 -b]pyridin-5 -yl)-oxazolo [5,4-b]pyridine,
5-Fluoro-2-[(3-methyl-3H-imidazol-4-yl)-pyridin-3-yl]-oxazolo[5,4-b]pyridine,
[5-(5-Fluoro-oxazolo[5,4-b]pyridin-2-yl)-3-methyl-pyridin-2-yl]-methyl-amine,
5-Fluoro-2-(1-methyl-1H-indazol-5-yl)-oxazolo[5,4-b] pyridine,
5-Fluoro-2-(1H-indo-6-yl)-oxazolo[5,4-b]pyridine,
5-Fluoro-2-(1-methyl-1H-pyrazolo[3,4-b]pyridin-5-yl)-oxazolo[5,4-b]pyridine,
2-(1,2-Dimethyl-1H-benzoimidazol-5-yl)-5-fluoro-oxazolo[5,4-b]pyridine,
5-Fluoro-2-(1-methyl-2,3-dihydro-1H-pyrrolo[2,3-b]pyridin-5-yl)-oxazolo[5,4-b]pyridine,
2-(3-Bromo-imidazo[1,2-a]pyridin-7-yl)-5-fluoro-oxazolo[5,4-b]pyridine,
5-Fluoro-2-(3-fluoro-1-methyl-1H-pyrrolo[2,3-b]pyridin-5-yl)-oxazolo[5,4-b]pyridine,
5-Fluoro-2-(1-methyl-1H-pyrrolo[2,3-b]pyridin-5-yl)-thiazolo[5,4-b]pyridine,
b 5-Fluoro-2-(1H-pyrrolo[2,3-b]pyridin-5-yl)-thiazolo[5,4-b]pyridine,
or a pharmaceutically acceptable salt, solvate or in vivo hydrolysable ester thereof.

8. The compound according to claim 7 which isotopically labeled as $^{11}$C, $^{13}$C, $^{14}$C, $^{18}$F, $^{15}$O, $^{13}$N, $^{35}$S, $^2$H, $^3$H.

9. The compound according to claim 7 which is 5-fluoro-2-(1H-indol-5-yl)[1,3]oxazolo[5,4-b]pyridine; or a pharmaceutically acceptable salt, solvate or in vivo hydrolysable ester thereof.

10. The compound according to claim 7 which is 5-fluoro-2-(1H-pyrrolo[2,3-b]pyridin-5-yl)[1,3]oxazolo[5,4-b]pyridine; or a pharmaceutically acceptable salt, solvate or in vivo hydrolysable ester thereof.

11. The compound according to claim 7 which is 5-Fluoro-2-(1-methyl-1H-pyrrolo[2,3-b]pyridin-5-yl)-oxazolo[5,4-b]pyridine; or a pharmaceutically acceptable salt, solvate or in vivo hydrolysable ester thereof.

12. The compound according to claim 7 which is 5-chloro-2-(1-methyl-1H-pyrrolo[2,3-b]pyridin-5-yl)-oxazolo[5,4-b]pyridine; or a pharmaceutically acceptable salt, solvate or in vivo hydrolysable ester thereof.

13. A pharmaceutical composition comprising a compound according to claim 1 and a pharmaceutically acceptable carrier.

* * * * *